(12) United States Patent
Yi et al.

(10) Patent No.: US 9,493,764 B2
(45) Date of Patent: Nov. 15, 2016

(54) HYBRID ELECTRONIC SHEETS

(71) Applicant: KOREA INSTITUTE OF SCIENCE AND TECHNOLOGY, Seoul (KR)

(72) Inventors: Hyunjung Yi, Seoul (KR); Ki Young Lee, Seoul (KR); Chaun Jang, Busan (KR); Joonyeon Chang, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 14/748,962

(22) Filed: Jun. 24, 2015

(65) Prior Publication Data

US 2015/0376596 A1 Dec. 31, 2015

Related U.S. Application Data

(63) Continuation-in-part of application No. 14/325,928, filed on Jul. 8, 2014, now Pat. No. 9,226,403.

(30) Foreign Application Priority Data

Apr. 22, 2014 (KR) .................. 10-2014-0048348
Mar. 11, 2015 (KR) .................. 10-2015-0034034

(51) Int. Cl.

| | | |
|---|---|---|
| *C12N 9/00* | (2006.01) | |
| *H05K 3/00* | (2006.01) | |
| *C12N 11/14* | (2006.01) | |
| *C12N 7/00* | (2006.01) | |

(Continued)

(52) U.S. Cl.
CPC .............. *C12N 11/14* (2013.01); *C12N 7/00* (2013.01); *C12N 9/0065* (2013.01); *H05K 3/007* (2013.01); *H05K 3/10* (2013.01); *B82Y 5/00* (2013.01); *C12N 2795/00031* (2013.01); *H05K 2203/0786* (2013.01); *H05K 2203/12* (2013.01); *H05K 2203/122* (2013.01); *H05K 2203/1305* (2013.01); *H05K 2203/1333* (2013.01)

(58) Field of Classification Search
CPC ................... C12N 11/14; C12N 7/00; C12N 2795/00031; H05K 3/007; H05K 3/10; H05K 2203/1333; H05K 2203/0786; H05K 2203/122; H05K 2203/12; H05K 2203/1305; B82Y 5/00

See application file for complete search history.

(56) References Cited

U.S. PATENT DOCUMENTS 5,212,290 A * 5/1993 Vogelstein ....... A61K 47/48561
530/387.1
7,473,411 B2 1/2009 Ajayan et al.

(Continued)

FOREIGN PATENT DOCUMENTS

| KR | 20080039869 A | 5/2008 |
|---|---|---|
| KR | 101188172 B1 | 9/2012 |

(Continued)

OTHER PUBLICATIONS

Cui et al., "Chemical Functionalization of Graphene Enabled by Phage Displayed Peptides", 2010, NANO letters, vol. 10, pp. 4559-4565, published on Oct. 13, 2010.*

(Continued)

*Primary Examiner* — Nikolay Yushin
(74) *Attorney, Agent, or Firm* — Ladas & Parry LLP

(57) ABSTRACT

Provided is an electronic sheet including a graphitic material and a phage which displays a peptide having a binding ability to the graphitic material on its coat protein or a fragment thereof.

20 Claims, 18 Drawing Sheets

(51) Int. Cl.
  *H05K 3/10* (2006.01)
  *C12N 9/08* (2006.01)
  *B82Y 5/00* (2011.01)

(56) References Cited

U.S. PATENT DOCUMENTS

| | | |
|---|---|---|
| 8,470,611 B2 | 6/2013 | Dang et al. |
| 2005/0086268 A1 | 4/2005 | Rogers |
| 2005/0147964 A1 | 7/2005 | Yamakawa et al. |
| 2005/0277160 A1 | 12/2005 | Shiba et al. |
| 2006/0073089 A1 | 4/2006 | Ajayan et al. |
| 2007/0117147 A1 | 5/2007 | Jagota et al. |
| 2010/0069606 A1 | 3/2010 | Bangera et al. |
| 2011/0070376 A1* | 3/2011 | Wales .................... A01N 63/00 427/414 |
| 2012/0156688 A1 | 6/2012 | McAlpine et al. |
| 2012/0178640 A1 | 7/2012 | Strano et al. |
| 2012/0255607 A1* | 10/2012 | Roy-Mayhew ...... H01G 9/2031 136/256 |
| 2013/0209807 A1 | 8/2013 | Chatterjee |
| 2013/0230464 A1 | 9/2013 | Yi et al. |
| 2014/0150855 A1 | 6/2014 | Inoue et al. |
| 2014/0197042 A1 | 7/2014 | Zhang et al. |
| 2014/0249052 A1 | 9/2014 | Mehmet et al. |
| 2014/0309126 A1 | 10/2014 | Yi et al. |
| 2015/0023858 A1* | 1/2015 | Tour ....................... C01B 21/064 423/276 |

FOREIGN PATENT DOCUMENTS

| | | |
|---|---|---|
| KR | 101325282 B1 | 10/2013 |
| WO | 2007/007154 A2 | 1/2007 |

OTHER PUBLICATIONS

Bunch et al., "Electromechanical Resonators from Graphene Sheets", 2007, Science, vol. 315, Issue 5811, pp. 490-493, published on Jan. 26, 2007.*

Bong Gill Choi, et al; "Solution Chemistry of Self-Assembled Graphene Nanohybrids for High-Performance Flexible Biosensors", ACS Nano, vol. 4, No. 5, Apr. 8, 2010, pp. 2910-2918.

Xiangnan Dang, et al; "Virus-templated self-assembled single-walled carbon nanotubes for highly efficient electron collection in photovoltaic devices", Nature Nanotechnology, vol. 6, pp. 377-384; Published online: Apr. 24, 2011.

Wenzhao Jia, et al; "Electrochemical Tattoo Biosensors for Real-Time Noninvasive Lactate Monitoring in Human Perspiration", Analytical Chemistry, vol. 85, Jul. 1, 2013, pp. 6553-6560.

Yun Jung Lee, et al; "Fabricating Genetically Engineered High-Power Lithium-Ion Batteries Using Multiple Virus Genes", Science, vol. 324, May 22, 2009; pp. 1051-1055.

Karen A. Noren, et al; "Construction of High-Complexity Combinatorial Phage Display Peptide Libraries", Methods, vol. 23, pp. 169-178, Feb. 2001.

Cheol-Hwan Park, et al; "Anisotropic behaviours of massless Dirac fermions in graphene under periodic potentials", Nature physics, vol. 4, pp. 213-217, Published online Feb. 24, 2008.

B.M. Paschal; "Direct Submission", Submitted Oct. 19, 2007 Research Department, New England Biolabs, 240 County Road, Ipswich, MA 10938, USA, 5 pages.

Seung-Wuk Lee, et al; "Chiral Smectic C. Structures of Virus-Based Films", Langmuir, vol. 19, pp. 1592-1598; Published on Web Dec. 24, 2002.

Sachdev S. Sidhu, et al; "High Copy Display of Large Proteins on Phage for Functional Selections", Journal Mol. Biol. vol. 296, pp. 487-495, Feb. 19, 2000.

Zhuangchun Wu et al; "Transparent, Conductive Carbon Nanotube Films", Science, vol. 305, Aug. 27, 2004, pp. 1273-1276.

Huanfen Yao, et al; "A contact lens with embedded sensor for monitoring tear glucose level", Biosensors and Bioelectronics, Dec. 31, 2010, vol. 26, pp. 3290-3296.

Hyunjung Yi, et al; "M13 Phage-Functionalized Single-Walled Carbon Nanotubes as Nanoprobes for Second Near-Infrared Window Fluorescence Imaging of Targeted Tumors", Nano Letters, vol. 12, pp. 1176-1183.

Michael B. Zwick, et al; "The Maltose-Binding Protein as a Scaffold for Monovalent Display of Peptides Derived from Phage Libraries", Analytical Biochemistry, vol. 264, pp. 87-97, Article No. AB982793, Nov. 1, 1998.

USPTO NFOA dated Apr. 16, 2015 in connection with U.S. Appl. No. 14/325,928.

* cited by examiner

HYBRID ELECTRONIC SHEETS

CROSS-REFERENCE TO RELATED APPLICATION

This application is a continuation-in-part of U.S. Ser. No. 14/325,928 filed Jul. 8, 2014; which claims the benefit of Korean Patent Application No. 10-2014-0048348, filed on Apr. 22, 2014, in the Korean Intellectual Property Office; and Korean Patent Application No. 10-2015-0034034, filed on Mar. 11, 2015, in the Korean Intellectual Property Office, the disclosures of which are incorporated herein in their entirety by reference.

BACKGROUND

1. Field

The present disclosure relates to a hybrid electronic sheet and a method for preparing the same.

2. Description of the Related Art

Researches on flexible high-performance materials and devices such as wearable computers, bendable displays, wearable biomedical electrodes and biosensors for health monitoring, human-robot interfaces, etc. are rapidly increasing nowadays. For such applications, development of a material which has excellent electrical property as well as superior mechanical property and to which biochemical or biological property can be further provided in addition to the electrical property, e.g., as in wearable biosensors, is of great importance. In addition, for realization of a high-performance device composed of various constituents on a flexible substrate, low contact resistance is required between the constituents and superior contact property with the flexible substrate is necessary.

Since carbon nanomaterials such as carbon nanotube, graphene, etc. have excellent electrical, mechanical and chemical properties, use of the materials as an electrode of flexible electronic devices, flexible bioelectrodes, sensors, flexible energy devices, etc. is actively studied recently.

For application of graphene or carbon nanotube to flexible devices, a process of transferring the graphene or carbon nanotube synthesized at high temperature without decrease in electrical property is essential. In addition, for effective operation of a high-performance device, effective electrical contact property between the carbon nanomaterial and other constituents of the device and resistance property on the flexible substrate are very important. Carbon nanotube is commonly used by depositing a film on a substrate, for example, by spin coating the carbon nanotube dispersed in an organic solvent or by forming a film through vacuum filtration and dissolving out the filter membrane chemically to obtain a carbon nanotube film. However, these methods are problematic in that the performance of the device is decreased or contact property with a flexible substrate is unsatisfactory due to an organic solvent or a dispersant remaining after chemical etching. Also, transfer onto a substrate with a complex shape is impossible because of large film thickness and patterning which is essential for realization of the device is difficult.

Graphene is used by growing the graphene on the surface of a metal such as copper by chemical vapor deposition (CVD) and transferring onto a desired substrate using an etching solution or by reducing chemically prepared graphene oxide through spin coating to obtain a reduced graphene oxide film. However, the CVD-grown graphene is disadvantageous in that use of an environmentally very harmful etching solution is necessary and effective surface area per unit area is very small because the graphene consists of a single or only a few layer(s). Further, because graphene is chemically stable, it is not easy to confer additional properties to the graphene. The reduced graphene oxide is disadvantageous in that electrical property is not excellent because a process of chemically reducing the graphene oxide which has been chemically oxidized is required.

When preparing a flexible electrode including a biomaterial such as a biosensor electrode, it is important to realize a high-performance flexible device without chemical etching. However, with the existing methods, it is difficult to realize a flexible device having superior electrical property wherein a biomaterial is nanohybridized.

SUMMARY

An aspect provides an electronic sheet including a graphitic material and a phage binding to the graphitic material, wherein a peptide is displayed on a coat protein of the phage or a fragment of the phage, and the binding occurs between the graphitic material and the peptide.

Another aspect provides an electrode or electronic device including the electronic sheet.

Still aspect provides a method of preparing a hybrid electronic sheet including: preparing a colloid material containing the graphitic material; adding the phage, which displays the peptide having a binding ability to the graphitic material on its coat protein or a fragment thereof, to a solution so as to prepare a phage solution; mixing the colloid material and the phage solution so as to prepare a mixture; and dialyzing the mixture using a membrane so as to form an electronic sheet in a solution.

An aspect provides an electronic sheet including a graphitic material and a phage binding to the graphitic material, in which the binding occurs between a peptide displayed on a coat protein of the phage or a fragment thereof and the graphitic material.

As used herein, the term "sheet" may refer to a material having a predetermined width and thickness, and for example, it is understood to include a film, a web, a membrane, or a complex structure thereof.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
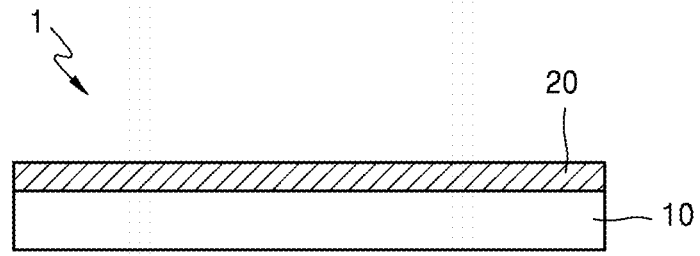
FIGS. 1A through 1D are schematic illustrations of an electrode including a hybrid electronic sheet according to an exemplary embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the exemplary embodiments are merely described below, by referring to the figures, to explain aspects of the present description.

As used herein, the term "graphitic material" may refer to a material having a surface with hexagonal arrangement of carbon atoms, i.e., a graphitic surface, and may include any graphitic material having the graphitic surface, regardless of physical, chemical or structural properties. Examples thereof may include a graphene sheet, a highly ordered pyrolytic graphite (HOPG) sheet, a carbon nanotube such as a single-walled carbon nanotube, a double-walled carbon nanotube, and a multi-walled carbon nanotube, or fullerene. The graphitic material may be a metallic, semiconductive, or hybrid material. For example, the graphitic material may be a mixture of a graphene sheet and a single-walled carbon nanotube.

In an exemplary embodiment, if the graphene sheet is used as the graphitic material, a two-dimensional structure of the graphene sheet allows a large contact area between constituent materials, compared to a material of one-dimensional structure. Therefore, it is possible to realize a large hybrid electronic sheet.

In another specific embodiment, if a mixture of the graphene sheet and the single-walled carbon nanotube is used as the graphitic material, the problem that a high concentration is necessary only when the graphene sheet is used may be solved while providing the advantage of two-dimensional structure of the graphene sheet.

In still another specific embodiment, if the graphene sheet is mixed with the single-walled carbon nanotube, the size and thickness of the sheet become larger and, in this case, the effective area of a nanoelectrode per unit area becomes large.

The peptide binding to the graphitic material may be a material capable of binding to the graphitic material in a nondestructive manner. The peptide may be selected from peptide libraries, for example, by a phage display technique. Through the phage display technique, the peptide may be genetically linked to, inserted into, or substituted for the coat protein of the phage, resulting in display of the protein on the exterior of phage, in which the peptide may be encoded by genetic information in the virion. Vast numbers of variants of the protein may be selected and screened by the displayed protein and DNA encoding the same, this method is called "biopanning". Briefly, biopanning is carried out by incubating the pool of phage-displayed variants with a target (e.g., graphitic material) that has been immobilized, washing away unbound phage, and eluting specifically bound phage by disrupting the binding interactions between the phage and the target. A portion of the eluted phage is set aside for DNA sequencing and peptide identification, and the remainder is amplified in vivo to prepare a sub-library for the next round. Then, this procedure is repeated.

The term "phage" or "bacteriophage" is used interchangeably, and may refer to a virus that infects bacteria and replicates within the bacteria. The phage or bacteriophage may be used to display a peptide which selectively or specifically binds to a graphitic material or volatile organic compound. The phage may be genetically engineered to display the peptide capable of binding to the graphitic material on a coat protein of the phage or a fragment thereof. As used herein, the term "genetic engineering" or "genetically engineered" means introduction of one or more genetic modifications into the phage in order to display the peptide capable of binding to the graphitic material on the coat protein of the phage or the fragment thereof, or a phage prepared thereby. The genetic modifications include introduction of a foreign gene encoding the peptide. The phage may be a filamentous phage, for example, M13 phage, F1 phage, Fd phage, If1 phage, Ike phage, Zj/Z phage, Ff phage, Xf phage, Pf1 phage, or Pf3 phage.

As used herein, the term "phage display" or "phage with a peptide displayed thereon" may refer to a display of a functional foreign peptide or protein on the surface of a phage or phagemid particle. The surface of the phage may refer to a coat protein of the phage or a fragment thereof.

The functional foreign peptide may be present as being linked to the N-terminus of the coat protein of the phage, or as being inserted into a coat protein. The phage may be a phage in which the C-terminus of the functional foreign peptide is linked to the N-terminus of the coat protein of the phage, or the peptide is inserted between consecutive amino acid sequences of the coat protein of the phage or replaced for a part of the consecutive amino acid sequences of the coat protein. The positions in the amino acid sequence of the coat protein, at which the peptide is inserted or replaced, may be positions of 1 to 5, positions of 1 to 40, positions of 1 to 30, positions of 1 to 20, position of 1 to 10, positions of 2 to 8, positions of 2 to 4, positions of 2 to 3, positions of 3 to 4, or a position of 2 from the N-terminus of the coat protein. Further, the coat protein may be p3, p6, p8 or p9.

The peptide having a binding affinity specifically to the graphitic material may be a peptide or a peptide set including one or more selected from the group consisting of amino acid sequences of $X_2SX_1AAX_2X_3P$ (SEQ ID NO. 1), $X_2X_2PX_3X_2AX_3P$ (SEQ ID NO. 2), $SX_1AAX_2X_3P$ (SEQ ID NO. 3) and $X_2PX_3X_2AX_3P$ (SEQ ID NO. 4). In some embodiments, the peptide or peptide set may include one or more selected from the group consisting of amino acid sequences of SEQ ID NOS. 5 to 8. Consecutive amino acid sequences of a coat protein of a phage may be linked to the N-terminus or C-terminus of the amino acid sequence of the peptide or peptide set. Therefore, for example, the peptide or peptide set may have an amino acid sequence having a length of 5 to 60, 7 to 55, 7 to 40, 7 to 30, 7 to 20, or 7 to 10 amino acids.

The peptide may have a conservative substitution of a known peptide. As used herein, the term "conservative substitution" denotes replacement of a first amino acid residue by a second different amino acid residue without changing biophysical properties of a protein or a peptide. Here, the first and second amino acid residues mean those having side chains having similar biophysical properties. The similar biophysical properties may include an ability to donate or accept hydrophobicity, charge, polarity, or hydrogen bonding. Examples of the conservative substitution may be within the groups of basic amino acids (arginine, lysine, and histidine), acidic amino acids (glutamic acid and aspartic acid), polar amino acids (glutamine and asparagine), hydrophobic amino acids (leucine, isoleucine, valine and methionine), hydrophilic amino acids (aspartic acid, glutamic acid, asparagine and glutamine), aromatic amino acids (phenylalanine, tryptophan, tyrosine and histidine), and small amino acids (glycine, alanine, serine and threonine). Amino acid substitutions that do not generally alter specific activity are known in the art. For example, in the peptide, X1 may be W, Y, F or H, X2 may be D, E, N or Q, and X3 may be I, L or V.

For example, the C-terminus of any one peptide of SEQ ID NO. 1 to SEQ ID NO. 8 may be linked to the body of M13 phage, that is, not to the tip of the phage, but to the N-terminus of p8 (SEQ ID NO. 19) having a length of 50 amino acids, which is present on the body in a longitudinal direction. Further, for example, any one peptide of SEQ ID NO. 1 to SEQ ID NO. 8 may be replaced for the positions of 2 to 4 (e.g., EGD), the positions of 2 to 3 or 3 to 4, or the position of 2 in the amino acid sequence of the coat protein p8 of M13 phage.

In an exemplary embodiment, a phage that displays a peptide having a binding affinity to a graphitic material may be a peptide or a peptide set specifically bind to the graphitic material, and thus additional functionalities may be provided by a non-destructive method of causing no damage to the properties of the graphitic material. In a case in which the peptide is displayed on the coat protein of the filamentous phage, a contact area with the graphitic material is large enough to provide a stronger binding affinity.

In another specific embodiment, the phage may be arranged on the graphitic surface with directionality using the filamentous structure of the phage itself. For example, it may be arranged in a row in a specific direction. In this case, the binding affinity of the peptide present on the coat protein of the phage for the graphitic surface is enhanced and the phage is arranged in a row. The phage arranged in a row may provide anisotropic functionality to the graphitic surface. In addition to the arrangement in a row, the phage may be arranged to form a structure having specific directionality, such as a layered (e.g., smectic), nematic, spiral or lattice structure. Accordingly, various functionalities may be provided onto the graphitic surface using the arrangement structures of the phage.

Further, the phage or peptide may be further bound with a biochemical enzyme in order to realize the electronic sheet as a biosensor. As used herein, the term "biochemical enzyme" may refer to an enzyme that specifically binds to a target material (e.g., an analyte or a material to be detected in sample) in order to realize a biosensor in an exemplary embodiment of the present invention. A proper biochemical enzyme may be selected by those skilled in the art, depending on the target material to be detected by the biosensor. The biochemical enzyme may include, for example, a protein, a peptide, a polypeptide, a low-molecular weight compound, a high-molecular weight compound, a nucleic acid, an aptamer, or an antisense nucleotide which is able to specifically bind to a substrate.

Further, the electronic sheet may be patterned by using a substrate or mask. The electronic sheet may be patterned by those skilled in the art, depending on the desired purpose. The electronic sheet according to an exemplary embodiment may be patterned without a chemical etching process.

The electronic sheet may have an area of, for example, 0.0001 to 1000 $cm^2$, 0.0001 to 100 $cm^2$, or 1 to 20 $cm^2$, and a thickness of, for example, 20 to 400 nm, 40 to 200, or 40 to 100 nm. Further, the internal structure of the electronic sheet may have a percolated network structure. As used herein, the term "percolated network" may refer to a lattice structure consisting of random conductive or non-conductive linkages.

Another aspect provides an electrode or electronic device, including the electronic sheet including the graphitic material and the phage binding to the graphitic material, in which the binding occurs between the peptide displayed on a coat protein of the phage or a fragment thereof and the graphitic material.

The electronic sheet is the same as described above.

The electronic device may refer to an electronic part using electrical conductivity, and a proper electronic device may be selected by those skilled in the art, depending on the desired use. The electronic device may include, for example, a transparent electronic device, a flexible electronic device, an information processing device, an information storing device, a biosensor device, a bioelectrode device, or an energy device.

Figure 1B:
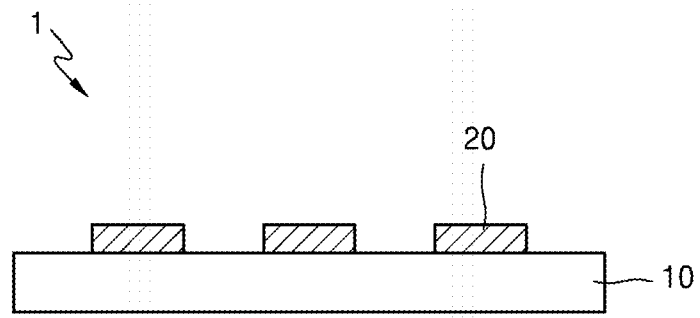
Figure 1C:
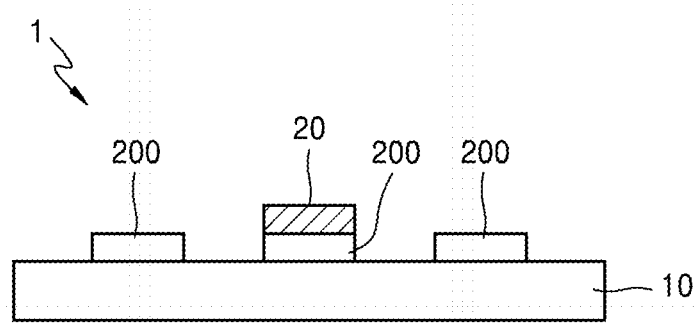
Figure 1D:
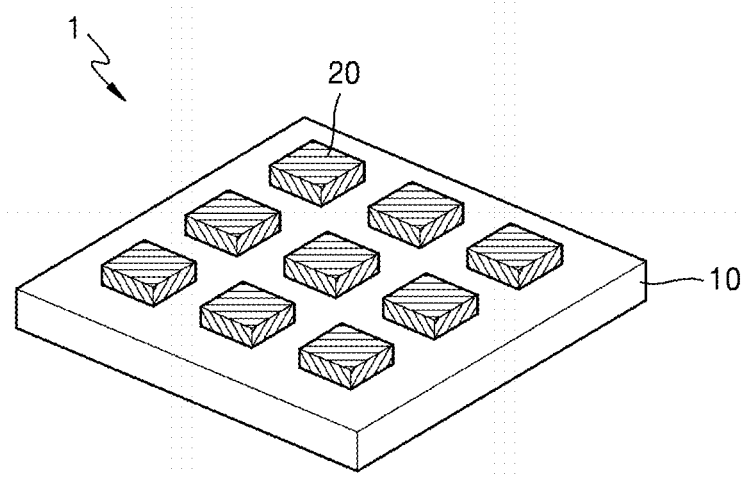

Referring to FIGS. 1A to 1D, the electrode or the electronic device may additionally include a substrate or a film. FIG. 1A is a view of an electrode in which a hybrid electronic sheet 20 is transferred on a substrate 10. FIG. 1B is a view of an electrode in which a pattern of the hybrid electronic sheet 20 is transferred on the substrate 10. FIG. 1C is a view of an electrode in which a pattern of a metal layer (for example, a platinum electrode) 200 is disposed on the substrate 10, and the hybrid electronic sheet 20 is disposed on the metal layer 200. FIG. 1D is a perspective view of an electrode in which the pattern of the hybrid electronic sheet 20 is transferred on the substrate 10.

One of ordinary skilled may select a suitable substrate or film according to purpose of an electrode or an electronic device. The substrate may be a conductive substrate or an insulating substrate. In some embodiments, the substrate may be an insulating substrate with at least one electrode thereon. The at least one electrode may include at least one electrode selected from a first electrode, a second electrode, and a third electrode. In some embodiments, the at least one electrode may include at least one electrode selected from a working electrode, an opposite electrode, and a reference electrode. The at least one electrode may further include, in addition to the working electrode, the opposite electrode, and the reference electrode, at least one electrode selected from an auxiliary electrode and a recognition electrode. In a case in which a graphitic material, to which the peptide or phage is bound, is disposed on an insulating substrate with at least one electrode thereon, the graphitic material may be disposed on a first electrode, or a working electrode, or a portion thereof.

Examples of the substrate may include a silver substrate, a silver epoxy substrate, a palladium substrate, a copper substrate, a gold substrate, a platinum substrate, a silver/silver chloride substrate, a silver/silver ion substrate, a mercury/mercury oxide substrate, a conductive carbon substrate, a semiconductor substrate, an oxide substrate, and a polymer substrate.

The substrate may be also a transparent flexible substrate. Examples of the transparent flexible substrate may include substrates that are manufactured from polydimethylsiloxane, PDMS), polyethersulfone (PES), poly(3,4-ethylenedioxythiophene), poly(styrenesulfonate), polyimide, polyurethane, polyester, perfluoropolyether (PFPE), polycarbonate, or combinations thereof.

Figure 2:
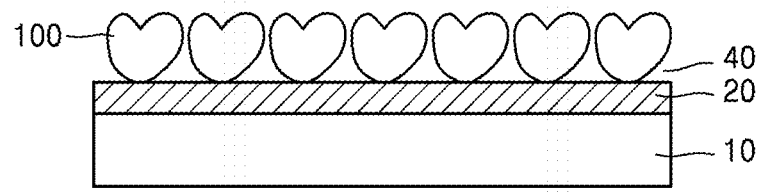
FIG. 2 is a schematic illustration of an electrode including the hybrid electronic sheet functionalized with a biochemical enzyme according to an exemplary embodiment.

Referring to FIG. 2, the electrode or electronic device may be functionalized using a biochemical enzyme 100 to be embodied as a biosensor electrode or device. FIG. 2 is a schematic view of a biosensor including a substrate 10, a hybrid electronic sheet 20, and an analyte binding layer 40 including the biochemical enzyme 100, which are sequentially stacked in this stated order. Descriptions of biochemical enzyme 100 are the same as presented above.

In an exemplary embodiment, since the hybrid electronic sheet is bound with the phage displaying the peptide having a nondestructive binding ability, it has superior electrical property and also semiconductor property, and if necessary, the property is controllable.

In another specific embodiment, since the hybrid electronic sheet is structurally stable, transparent, and flexible, it may be transferred to various substrates or non-conventional substrates, and various patterns may be also formed thereon using a substrate or a mask.

In still another specific embodiment, since the hybrid electronic sheet is hybridized with the phage, it is highly compatible with biomaterials, and it may be further functionalized with other biomaterials.

Therefore, the electronic sheet according to an exemplary embodiment may be usefully applied to an electrode, for example, a brain surface electrode, or an electronic device, such as a transparent electronic device, a flexible electronic device, an information processing device, an information storing device, a biosensor device, a bioelectrode device or an energy device.

Another aspect provides a method of preparing the electronic sheet including: preparing a colloid material containing the graphitic material; adding the phage, which displays the peptide having a binding ability to the graphitic material on its coat protein or a fragment thereof, to a solution so as to prepare a phage solution; mixing the colloid material and the phage solution so as to prepare a mixture; and dialyzing the mixture using a membrane so as to form an electronic sheet in a solution.

In preparing the colloid material, the colloid material may be an aqueous solution, in which graphitic materials are dispersed or dissolved. The colloid material may be prepared by stabilizing the graphitic materials in a surfactant-containing solution.

Further, the surfactant may include a surfactant which is bio-compatible with biomaterials such as the peptide or phage. Example thereof may include sodium cholate, SDS (sodium dodecyl sulfate), DOC (sodium deoxycholate), Nonidet P-40, Triton X-100, or Tween 20®.

In preparing the phage solution, the method of preparing the phage is the same as described above. Further, the prepared phage may be added to an appropriate solution, for example, distilled water, phosphate-buffered saline (PBS), or Tris-buffered saline (TBS), and the solution may have pH of 5 to 8.

In preparing the mixture, a mixing ratio of the colloid material and the phage solution may be controlled by those skilled in the art, depending on use of the electronic sheet. That is, it may be controlled depending on the desired properties of the electronic sheet, such as electrical conductivity, electrical conductive property, electrochemical charging current, hydrophilicity, etc. For example, the molar ratio of the colloid material and the phage solution may be controlled in terms of structural stability of the electronic sheet, formation of the electronic sheet with a large area, and electrical resistance of the electronic sheet. The molar ratio may be a molar ratio of 30:1 to 1:30, a molar ratio of 20:1 to 1:20, a molar ratio of 15:1 to 1:15, a molar ratio of 10:1 to 1:10, or a molar ratio of 8:1 to 1:8, for example, 20:1, 10:1, 4:1, 1:4, or 1:8.

In an exemplary embodiment, when the colloid material and the phage solution are mixed at a predetermined molar ratio, charging current of the electronic sheet may be improved, and network formation of the graphitic material in the hybrid electronic sheet may be controlled.

In another specific embodiment, when a hybrid single-walled carbon nanotube which is not electrically isolated is used, a p-type semiconductor property may be obtained by controlling the molar ratio of the colloid material and the phage solution. That is, a semiconductor or metallic hybrid electronic sheet may be obtained by controlling the molar ratio of the colloid material containing the graphitic material and phage solution.

Forming the electronic sheet by dialysis may include dialyzing a membrane tube to which the mixture has been added against the dialysis solution or dialyzing the mixture using the membrane itself. The membrane may include a membrane or material capable of dialyzing the mixture, which has semipermeable property. For example, forming the electronic sheet by dialysis may be to conduct dialysis in a solution to which ions have been added. The concentration of the ions contained in the dialysis solution may be in the range from 0 or higher to lower than 10 mM. The concentration of the ions may be controlled by adding a monovalent electrolyte to the dialysis solution. For example, 0.1 mM NaCl may be added to triple distilled water.

Further, the dialysis solution may be distilled water, triple distilled water (resistance>18 Mohm cm), PBS, or TBS in terms of the stability with the phage.

In forming the electronic sheet by dialysis, the dialysis may be performed for about 5 to 60 hours, about 10 to 50 hours, or about 15 to 40 hours. After the dialysis, a thin electronic sheet may be formed along the surface of the membrane tube.

Further, the method of preparing the electronic sheet may further include, after forming the electronic sheet by dialysis, separating the formed electronic sheet in an aqueous solution. The separation may be accomplished, for example, by twisting the membrane tube used for the dialysis to separate the electronic sheet formed along the membrane. A freestanding electronic sheet may be obtained by controlling the membrane clip in an aqueous solution.

Further, the method of preparing the electronic sheet may further include replicating the electronic sheet formed in the aqueous solution using a suitable substrate or mask according to its use. The substrate or mask may be made of a metal, a semiconductor, an insulator, a polymer, an elastomer, etc. For example, a flexible electronic device may be prepared by replicating the electronic sheet using a flexible polymer substrate. Further, this process is to form patterns on the electronic sheet by replicating the separated electronic sheet using a patterned substrate or mask. For example, if a patterned stencil mask is used, the pattern is formed on the electronic sheet when the mask is detached after the electronic sheet is completely dried. By this process, a device may be realized on a flexible electronic sheet without additional physical or chemical etching.

In an exemplary embodiment, the method of preparing the electronic sheet may be used to prepare a nanostructure in which the graphitic material and the phage are uniformly dispersed. As a result, it is possible to prepare a large-area, flexible electronic sheet having a thickness of 400 nm or smaller and an area of tens of $cm^2$.

In another specific embodiment, when the method of preparing the electronic sheet is used, no chemical etching or no additional carrier material layer is necessary for transference of various substrates.

In still another specific embodiment, when the method of preparing the electronic sheet is used, patterning may be easily conducted using a substrate or a mask.

Hereinafter, the present invention will be described in more detail with reference to Examples. However, these Examples are for illustrative purposes only, and the invention is not intended to be limited by these Examples.

Example 1

Preparation and Characterization of Hybrid Electronic Sheet

1. Preparation of Hybrid Electronic Sheet 1
1.1. Preparation of Colloid Solution First, an aqueous solution is prepared by adding 2% w/v sodium cholate as a surfactant to distilled water, and a colloid solution is prepared by stabilizing single-walled carbon nanotube with the sodium cholate by dialysis of carbon nanotube (manufacturer: Nanointegris, SuperPure SWNTs, solution-type, concentration: 250 mg/ml) for 48 hours.

In this regard, assuming that an average length and an average diameter of the carbon nanotube (CNT) are 1 μm and 1.4 nm, respectively, the number of the single-walled carbon nanotube included in the colloid solution may be calculated according to the following equation.

Number of single-walled carbon nanotube(number/mL)=concentration (μg/mL)×3×10$^{11}$ CNT   [Equation 1]

According to this Equation, the number of the single-walled carbon nanotube included in the colloid solution is calculated as $7.5 \times 10^{13}$/mL.

1.2. Preparation of Phage Displaying Peptide having Binding Ability to Graphitic Material As M13 phages having a strong binding affinity to the graphitic surface, M13 phage (p8GB#1) displaying a peptide DSWAADIP (SEQ ID NO. 5) having a strong binding affinity to the graphitic surface and M13 phage (p8GB#5) displaying a peptide DNPIQAVP (SEQ ID NO. 6) are prepared by the following method.

First, an M13HK vector is prepared using oligonucleotides of SEQ ID NOS. 10 and 11 for site-directed mutation of the 1381$^{st}$ base pair C of an M13KE vector (NEB, product #N0316S) (SEQ ID NO. 9) to G. The prepared M13HK vector is double-digested using restriction enzymes, BspHI (NEB, product #R0517S) and BamHI (NEB, product #R3136T), and dephosphorylated using antarctic phosphatase. The dephosphorylated vector is ligated to a double-digested DNA duplex by incubation at 16° C. overnight. A product is then purified and concentrated. Electorcompetent cells (XL-1 Blue, Stratagene) are transformed with 2 μl of a concentrated ligated vector solution by electroporation at 18 kV/cml. A total of five transformations are performed for the library construction. Then, the transformed cells are incubated for 60 minutes, and fractions of several transformants are plated onto agar plates containing x-gal/isopropyl-β-D-1-thiogalactopyranoside (IPTG)/tetracycline (Tet) to determine the diversity of the library. The remaining cells are amplified in a shaking incubator for 8 hours. Oligonucleotides of SEQ ID NOS. 12 and 13 are used in construction of the phage-display p8 peptide library.

The base sequences of the phage-display p8 peptide library constructed according to an exemplary embodiment have diversity of $4.8 \times 10^7$ pfu (plaque forming unit), and include approximately $1.3 \times 10^5$ copies of each sequence.

Then, a highly ordered pyrolytic graphite (HOPG) substrate (manufacturer: SPI product #439HP-AB) having a diameter of 1 cm was prepared. In this regard, the HOPG substrate is a HOPG substrate having a relatively large grain size of 100 μm or smaller. Previously, a carbon nanotube film surface damaged during its production process has been generally used as a graphitic surface, and thus it is difficult to identify peptides having high binding affinity. In order to solve this problem, a fresh surface is detached from HOPG as a material having a graphitic surface using a tape immediately before use, so as to minimize the defect of the sample surface due to, for example, oxidation. Subsequently, the phage display p8 peptide library of $4.8 \times 10^{10}$ pfu ($4.8 \times 10^7$ diversities, 1000 copies per each sequence) prepared in 1 of Example 1 is prepared in 100 μL of Tris-buffered saline (TBS) and conjugated with the HOPG surface for 1 hour in a shaking incubator at 100 rpm. 1 hour later, the solution is removed and the surface is washed 10 times in TBS. The washed HOPG surface is reacted with Tris-HCl of pH 2.2 as an acidic buffer for 8 minutes to elute peptides reacting non-selectively, and the remaining phage was eluted with an XL-1 blue *E. coli* culture in mid-log phase for 30 minutes. A portion of the eluted culture is set aside for DNA sequencing and peptide identification, and the remainder is amplified to prepare a sub-library for the next round. The above procedure is repeated using the prepared sub-library. Meanwhile, the left plaque is subjected to DNA sequencing to obtain the p8 peptide sequence, and the sequence is analyzed to obtain a phage (P8GB#1) with DSWAADIP (SEQ ID NO: 5) displayed thereon and a phage (p8GB#5) with DNPIQAVP (SEQ ID NO: 6) displayed thereon. Herein, DSWAADIP (SEQ ID NO: 5) and DNPIQAVP (SEQ ID NO: 6) are peptide sequences having a strong binding affinity to a graphitic material.

1.3. Preparation of Hybrid Electronic Sheet 1.3.1. Preparation of Phage-Bound Hybrid Electronic Sheet The colloid solution prepared above and a phage solution containing the M13 phage (p8GB#1) having strong affinity to the graphitic material are mixed at a molar ratio of 4:1, 10:1, 20:1, 1:2, 1:4, and 1:8.

Figure 4A:
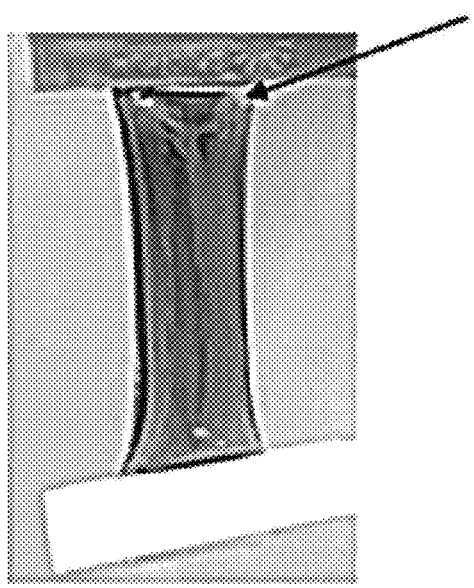
FIG. 4A is an image showing formation of the hybrid electronic sheet according to an exemplary embodiment.
Figure 4B:
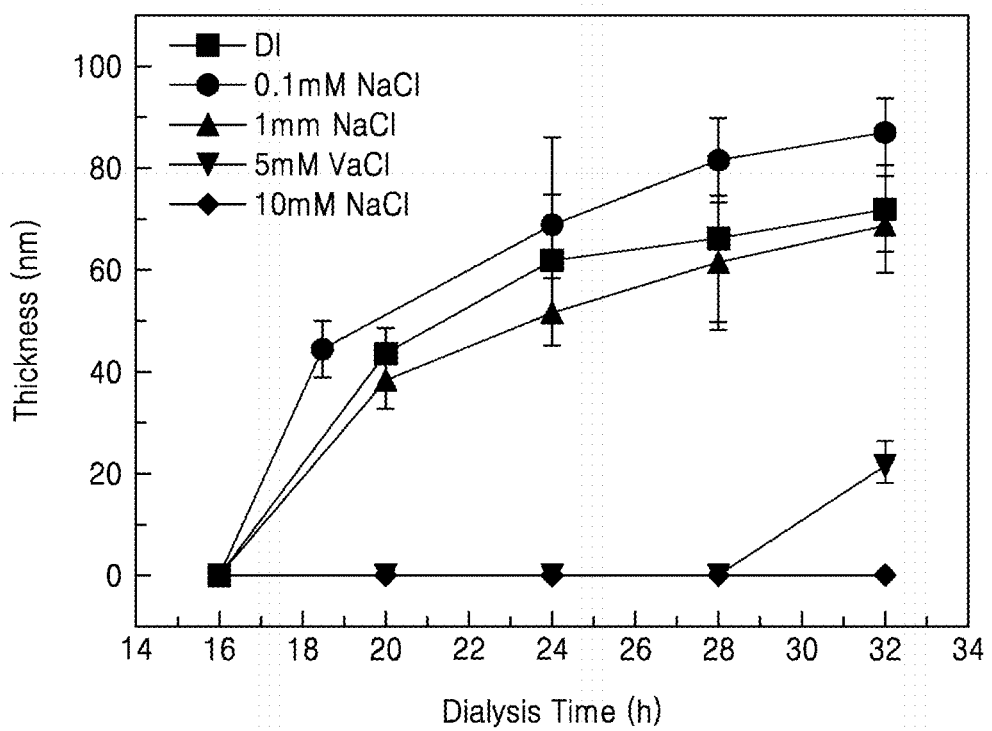
FIG. 4B is a graph showing the dependency of hybrid electronic sheet formation on the ionic strength of a dialysis solution according to an exemplary embodiment.

Next, for dialysis, each of the mixtures is added to a semipermeable dialysis membrane (SpectrumLab, MWCO 12,000~14,000, product #132 700) tube, and each membrane tube is dialyzed against triple distilled water having ion concentration (NaCl) of 0.1 mM, 1 mM, 5 mM, and 10 mM. About 16 hours, a thin electronic sheet is formed along the surface of the membrane tube. FIG. 4A shows an image of the electronic sheet formed at a molar ratio of 4:1 from among the formed electronic sheets. FIG. 4B is a graph showing the dependency of hybrid electronic sheet formation on the ionic strength of a dialysis solution according to an exemplary embodiment.

Figure 5:
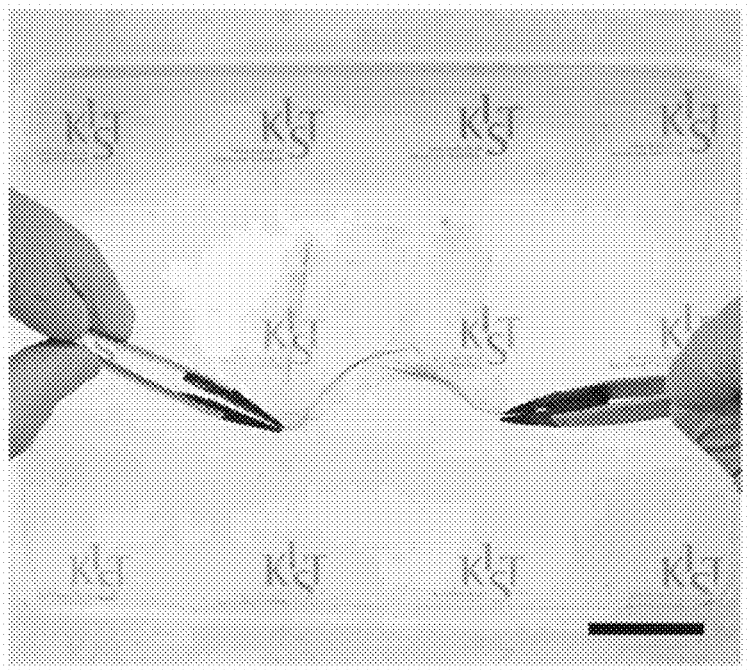
FIG. 5 is an image of a large-area freestanding hybrid electronic sheet according to an exemplary embodiment.

Next, each membrane tube is transferred to triple distilled water and the electronic sheet is detached by twisting the membrane of the membrane tube and then dried. FIG. 5 shows an image of the electronic sheet formed at a molar ratio of 4:1 from among the formed electronic sheets. The electronic sheet thus prepared has a thickness of about 100 nm.

Figure 3A:
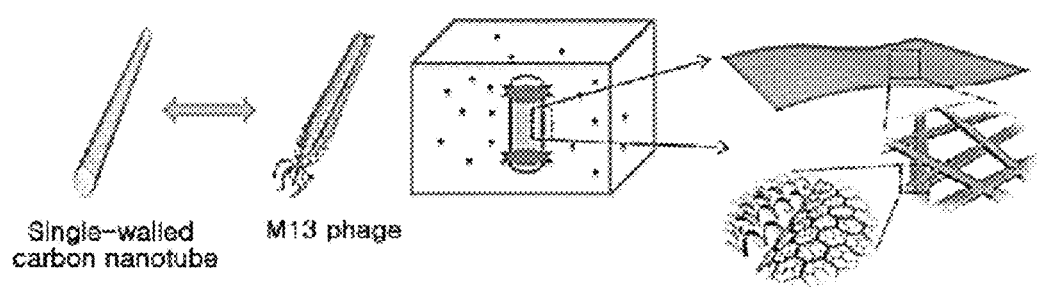
FIG. 3A is a schematic illustration of a production process of the hybrid electronic sheet according to an exemplary embodiment.

FIG. 3A is a schematic illustration of a production process of the hybrid electronic sheet according to an exemplary embodiment.

As shown in FIG. 3A, carbon nanotube is dispersed or dissolved in the colloid material which is stabilized by adding it to the surfactant-containing solution. Single-walled carbon nanotube is bound with about one M13 phage finally to form a sheet having a percolated network structure of carbon nanotube and M13 phage.

Figure 3B:
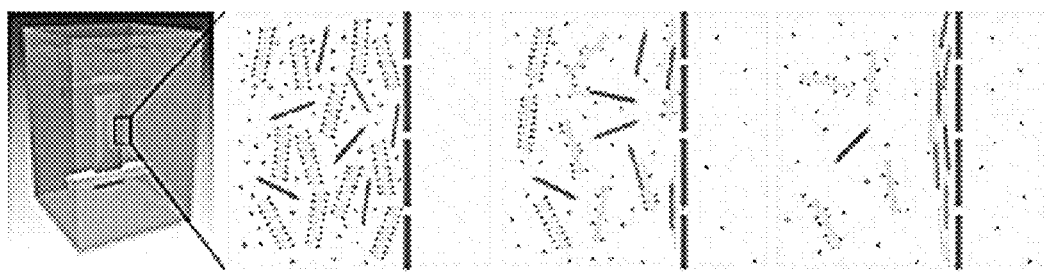
FIG. 3B is a schematic illustration of a formation principle of the hybrid electronic sheet according to an exemplary embodiment.

FIG. 3B is a schematic illustration of a formation principle of the hybrid electronic sheet according to an exemplary embodiment.

Figure 3C:
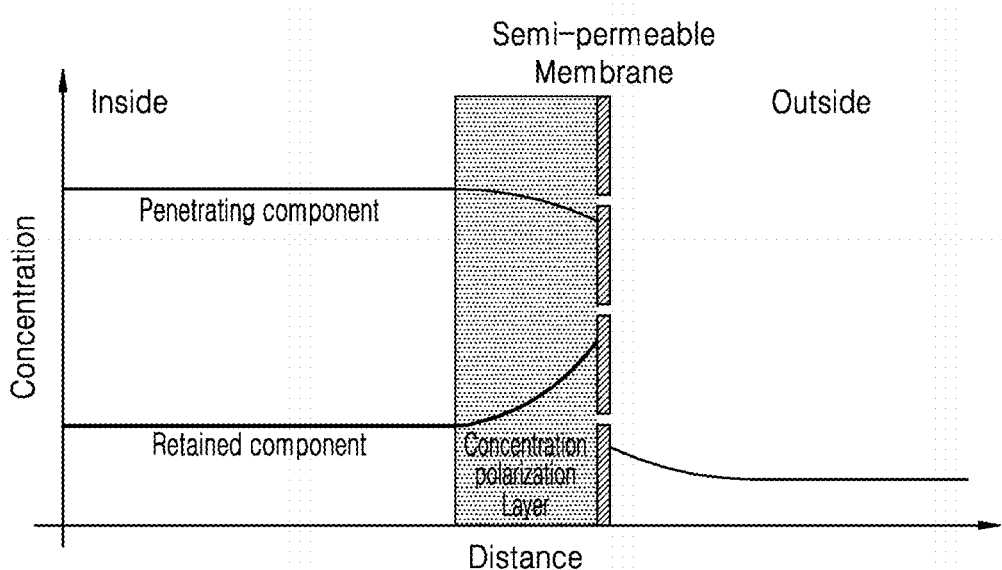
FIG. 3C is a graph showing concentration polarization in the formation principle of the hybrid electronic sheet according to an exemplary embodiment.

FIG. 3C is a graph showing concentration polarization in the formation principle of the hybrid electronic sheet according to an exemplary embodiment.

Referring to FIGS. 3B and 3C, formation of the carbon nanotube bound with M13 phage displaying the peptide according to an exemplary embodiment may be achieved by adding the mixture of the phage solution and the colloid solution to the membrane tube, followed by dialysis against the dialysis solution. While the dialysis proceeds, the concentration of the surfactant, which is attached on the surface of the carbon nanotube in the colloid material and stabilizes the carbonaceous material, in the tube decreases due to diffusion owing to a concentration difference inside and outside the membrane. This diffusion-driven dilution is the most prominent near the membrane. Since the M13 phage displaying the peptide having strong binding affinity to carbon nanotube can begin reacting with the carbon nanotube only when the concentration of the surfactant surrounding the carbon nanotube is low, the binding occurs near the membrane where the dilution occurs the most actively, when the dialysis proceeds for a predetermined time. Based on this principle, a sheet may be formed through dialysis.

FIG. 4A is an image showing formation of the hybrid electronic sheet according to an exemplary embodiment.

As shown in FIG. 4A, it is confirmed that a thin electronic sheet is formed. The formation principle for the thin electronic sheet is already described above.

FIG. 4B a graph showing the dependency of hybrid electronic sheet formation on the ionic strength of a dialysis solution according to an exemplary embodiment.

As shown in FIG. 4B, in the case of distilled water (DI) having an ion concentration of 0 and DI having an ion concentration of 0.1 mM, an electronic sheet was normally formed; however, in the case of DI having an ion concentration of 10 mM, an electronic sheet was not formed well. From these results, it was confirmed that since a higher ion concentration results in a decrease in stabilizing effects of a surfactant adsorbed to carbon nanotube, in the membrane, carbon nanotubes aggregate, or the aggregation occurs seriously without the formation of a sheet. In a case in which the ion concentration is 0 or at a certain level, carbon nanotubes showing a negative (−) charge due to absorption of a surfactant have a strong electric repulsive force against each other, and accordingly, during a sheet is formed along the membrane due to the strong binding affinity between the phage and carbon nanotubes, the well dispersion state of carbon nanotubes is maintained inside the membrane tube, leading to a continuous formation of the sheet.

1.3.2. Preparation of Non-Phage-Bound Hybrid Electronic Sheet

As Comparative Example of the present invention, an electronic sheet including no phage is prepared by the following method.

Figure 6:
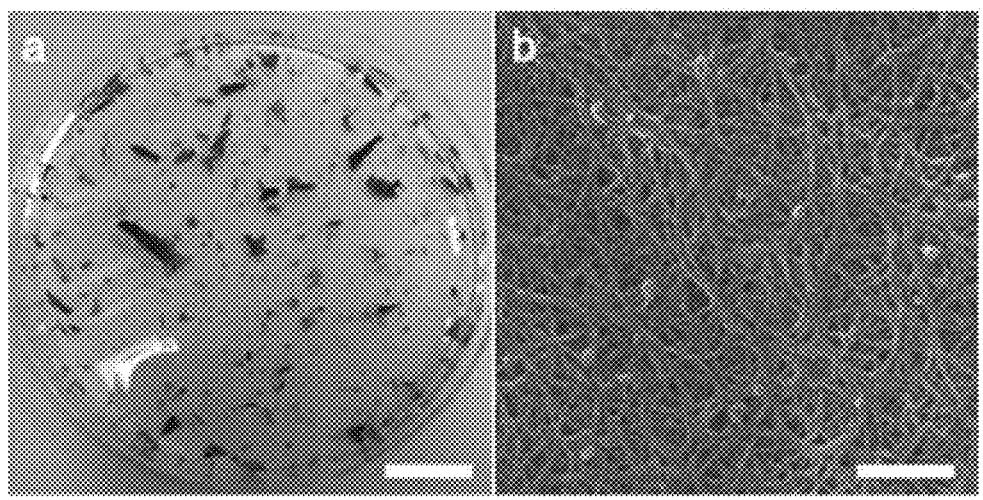
FIG. 6 is an image of a sample having only a single-walled carbon nanotube without a phage.
Figure 7:
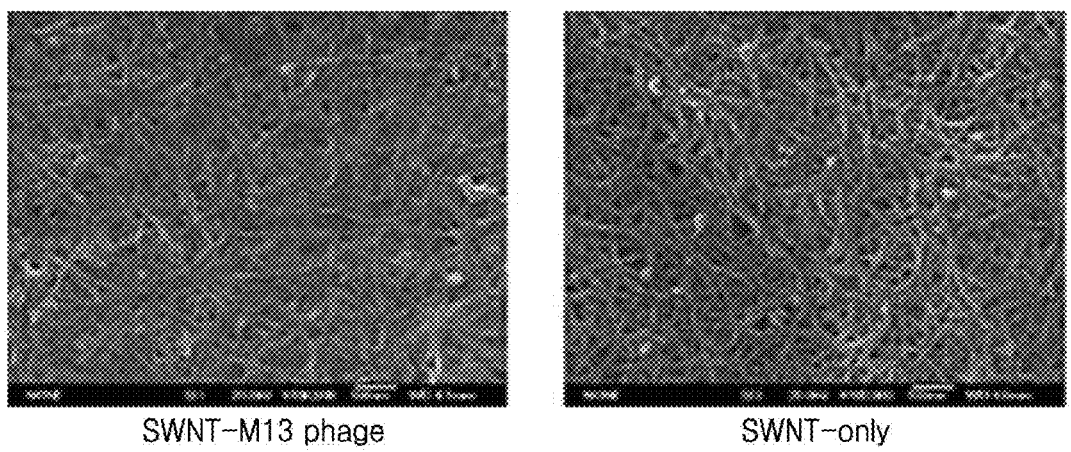
FIG. 7 is a scanning electron microscopic (SEM) image showing a nanostructure of a phage-bound hybrid electronic sheet according to an exemplary embodiment and a nanostructure of a non-phage bound electronic sheet.

First, an aqueous solution is prepared by adding 2% w/v sodium cholate as a surfactant to distilled water, and a colloid solution is prepared by stabilizing a single-walled carbon nanotube (manufacturer: Nanointegris, SuperPure SWNTs, solution-type, concentration: 250 µg/ml) with the sodium cholate by dialysis of the single-walled carbon nanotube as the graphitic material for 48 hours. Next, for dialysis, 0.4 mL of the colloid solution diluted with 10 mL of 1% w/v sodium cholate aqueous solution is added to a semipermeable dialysis membrane (SpectrumLab, MWCO 12,000~14,000, product #132 700) tube, and the membrane tube is dialyzed against triple distilled water. About 24 hours after the dialysis, an electronic sheet is formed along the surface of the membrane tube. Next, the membrane tube is transferred to triple distilled water and the electronic sheet is detached by twisting the membrane of the membrane tube. FIG. 6 shows a photograph and a scanning electron microscopic (SEM) image of the detached electronic sheet, compared with the phage-bound hybrid electronic sheet of FIG. 5. Further, SEM images of nanostructures of the phage-bound hybrid electronic sheet and the non-phage-bound electronic sheet are compared and the result is shown in FIG. 7.

FIG. 5 is an image of a large-area freestanding hybrid electronic sheet according to an exemplary embodiment.

FIG. 6 is an image of a sample having only a single-walled carbon nanotube without a phage.

As shown in FIG. 5, the phage-bound hybrid electronic sheet according to an exemplary embodiment is stably formed with a large area due to binding of the carbon nanotube and the phage and has a nanostructure in which the carbon nanotubes are uniformly distributed. In contrast, as shown in FIG. 6, non-phage-bound electronic sheet is broken into pieces during the preparation process and has a microstructure with bundling. These results indicate that the freestanding phage-bound hybrid electronic sheet according to an exemplary embodiment maintains its shape owing to the strong binding affinity between the carbon nanotube and the phage, whereas the electronic sheet is formed along the membrane but broken easily when dialysis is performed without addition of the phage, which is a limitation in its application.

FIG. 7 shows SEM images of the nanostructure of the phage-bound hybrid electronic sheet according to an exemplary embodiment and the nanostructure of the non-phage bound electronic sheet.

As shown in FIG. 7, the non-phage-bound electronic sheet shows severe bundling due to aggregation of single-walled carbon nanotubes whereas the phage-bound hybrid electronic sheet according to an exemplary embodiment has a nanostructure in which the phage is strongly bound to the single-walled carbon nanotube and uniformly distributed.

1.4. Preparation of Hybrid Electronic Sheet Transferred onto Substrate and Patterning of Hybrid Electronic Sheet Using Stencil Mask The hybrid electronic sheet prepared by mixing at a molar ratio of 4:1 in Example 1.3.1 is replicated and transferred onto a polymer (PES; polyethersulfone) substrate, and a hybrid sheet on PES is photographed and shown in FIG. 8A. Additionally, the hybrid electronic sheet prepared by mixing at a molar ratio of 4:1 is replicated and transferred onto a plastic with a complex shape, and then photographed and shown in FIG. 8B.

Figure 9:
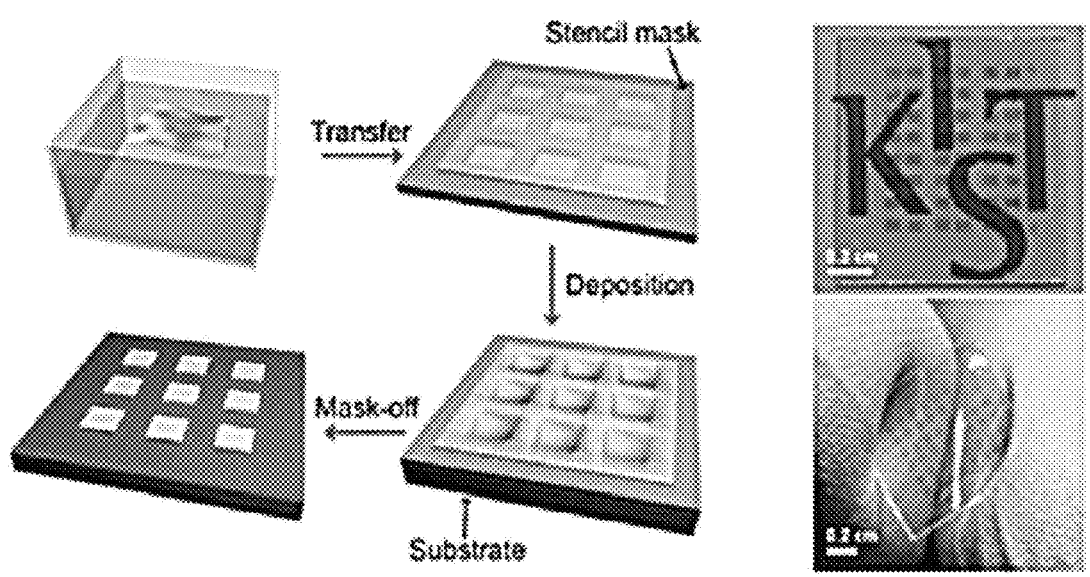
FIG. 9 is a schematic illustration of a method of patterning a hybrid electronic sheet using a stencil mask according to an exemplary embodiment and an image of the patterned hybrid electronic sheet.

Furthermore, patterning of the hybrid electronic sheet is performed using a stencil mask. In detail, the hybrid electronic sheet prepared by mixing at a molar ratio of 4:1 in Example 1.3.1 is transferred to a stencil mask, and then deposited on a $SiO_2$(300 nm)/Si substrate (manufacturer: SILTRON INC, product name: EPI-Prime Si wafer). The hybrid electronic sheet transferred onto the substrate is washed with deionized water after removing the stencil mask, and then dried using nitrogen gas so as to prepare a patterned hybrid electronic sheet. A formation process thereof and an image thereof are shown in FIG. 9.

Figure 8A:
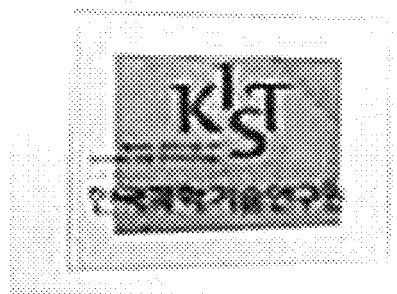
FIG. 8A is an image of the hybrid electronic sheet according to an exemplary embodiment which is transferred onto a PES polymer substrate.

FIG. 8A is an image of the hybrid electronic sheet according to an exemplary embodiment which is transferred onto the PES polymer substrate.

Figure 8B:
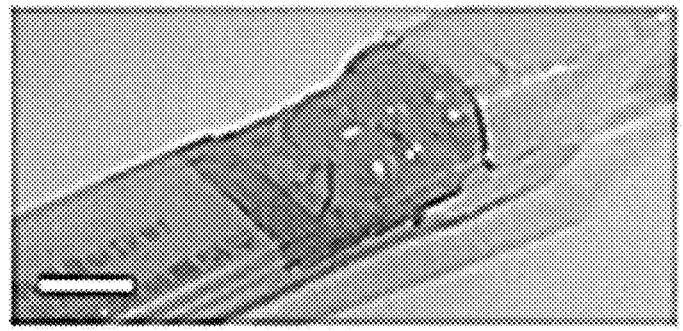
FIG. 8B is an image of the hybrid electronic sheet according to an exemplary embodiment which is transferred onto a plastic substrate with a complex shape.

FIG. 8B is an image of the hybrid electronic sheet according to an exemplary embodiment which is transferred onto the plastic substrate with a complex shape.

As shown in FIGS. 8A through 8B, the preparation method of the hybrid electronic sheet according to an exemplary embodiment is used to prepare an aqueous solution by dialysis of the mixture of the carbon nanotube and the phage using the membrane, and thus no chemical etching or additional carrier material layer is necessary for transference. Accordingly, it is possible to transfer the sheet onto various substrates including a polymer material with a complex shape.

FIG. 9 is a schematic illustration of a method of patterning the hybrid electronic sheet using a stencil mask according to an exemplary embodiment and an image of the patterned hybrid electronic sheet.

As shown in FIG. 9, since the hybrid electronic sheet according to an exemplary embodiment is transparent and flexible, various patterns may be formed thereon, and thus the sheet may be usefully applied to a transparent device and a flexible device.

1.5. Analysis of Hydrophilic Property of Hybrid Electronic Sheet Transferred on Substrate In order to analyze hydrophilic property of the hybrid electronic sheet transferred onto the substrate, the hybrid electronic sheets prepared by mixing at a molar ratio of 4:1, 10:1, or 20:1 in Example 1.3.1 are transferred onto a polymer (PES; polyethersulfone) substrate, and their hydrophilic property is compared with that of the polymer substrate not transferred (bare PES polymer). After dropping 20 mL of distilled water on the substrate onto which the respective electronic sheets have been transferred, contact angles are measured 5 minutes later to compare hydrophilic property. The result is shown in FIG. 10.

Figure 10:
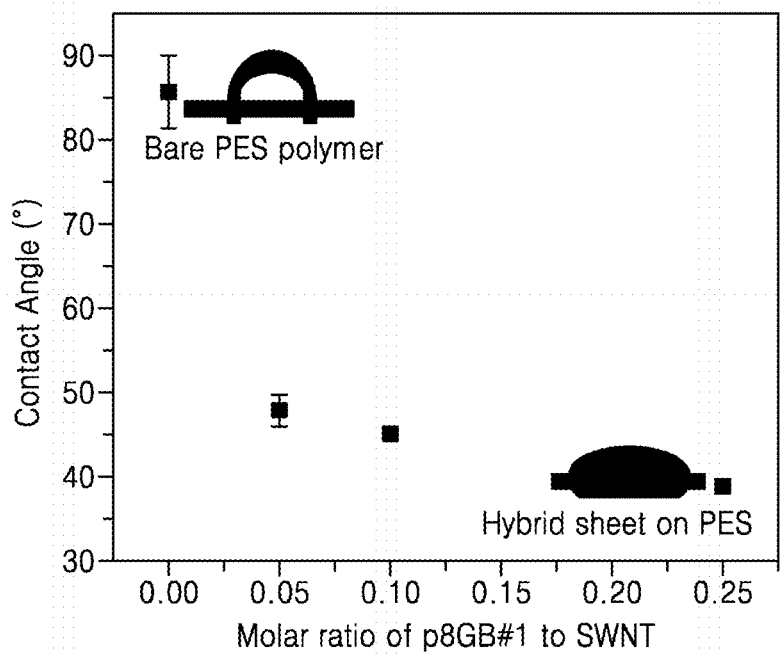
FIG. 10 is a graph showing a result of measuring contact angles to compare the change in hydrophilic property of the electronic sheet according to an exemplary embodiment depending on a molar ratio (SWNT:p8GB#1=4:1, 10:1, 20:1) of a single-walled carbon nanotube and a phage (p8GB#1) in the hybrid electronic sheet.

FIG. 10 is a graph showing a result of measuring contact angles to compare the change in hydrophilic property of the electronic sheet according to an exemplary embodiment depending on a molar ratio (SWNT:p8GB#1=4:1, 10:1, 20:1) of a single-walled carbon nanotube and a phage (p8GB#1).

As shown in FIG. 10, when the phage-bound carbon nanotube according to an exemplary embodiment is transferred onto the polymer substrate (hybrid sheet on PES), the contact angle is about 2-3 times smaller than that of the bare PES polymer. Accordingly, this result indicates that the hybrid electronic sheet according to an exemplary embodiment has high hydrophilicity.

1.6. Comparison of Electrochemical Property of Hybrid Electronic Sheet Transferred onto Substrate The hybrid electronic sheet prepared by mixing at a molar ratio of 4:1 in Example 1.3.1 is transferred onto a polymer (PES) substrate and a gold (Au) film, and their charging current (current density) is compared as follows.

The charging current is measured using a potentiostat/galvanostat (VersaStat 3, Princeton Applied Research (PAR)). Pt wire and Ag/AgCl (3 M KCl saturated, K0260, PAR) is used as a counter electrode (PAR, K0266) and a reference electrode, respectively, and phosphate-buffered saline (PBS; 0.1 M phosphate, 100 mM phosphate, pH=7.4) is used as an electrolyte. The measurement is made in a voltage range of 0~0.6 V at a scan rate of 250 mV/s. The result is shown in FIG. 11.

Figure 11:
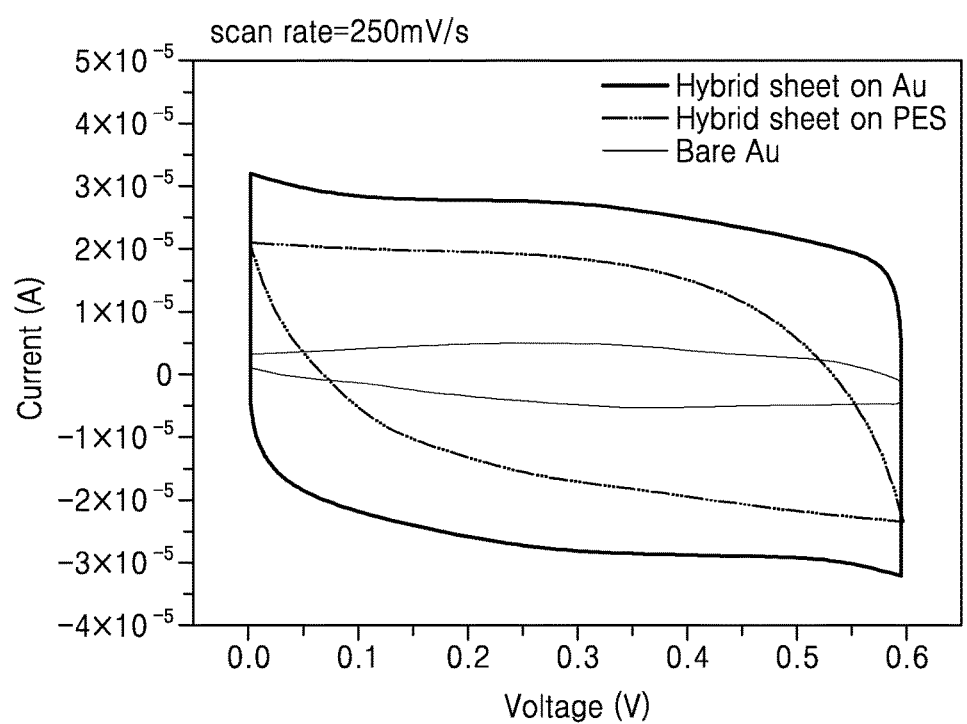
FIG. 11 is a graph showing electrochemical conductivity of the hybrid electronic sheet according to an exemplary embodiment.

FIG. 11 is a graph showing electrochemical conductivity of the hybrid electronic sheet according to an exemplary embodiment.

As shown in FIG. 11, since higher charging current for the sample area indicates better conductivity and good formation of a nanostructure, the hybrid electronic sheet according to an exemplary embodiment exhibits superior conductivity and has a well-defined nanostructure. In addition, the fact that the hybrid electronic sheet exhibits about 4 times higher charging current on a transparent insulating polymer substrate without a metal film (hybrid sheet on PES) than on a metal film (bare Au) shows that the hybrid electronic sheet according to an exemplary embodiment may also be used for electrochemical electrodes which require not only flexibility but also transparency.

1.7 Comparison of Electrical Conductivity of Hybrid Electronic Sheet

Figure 12:
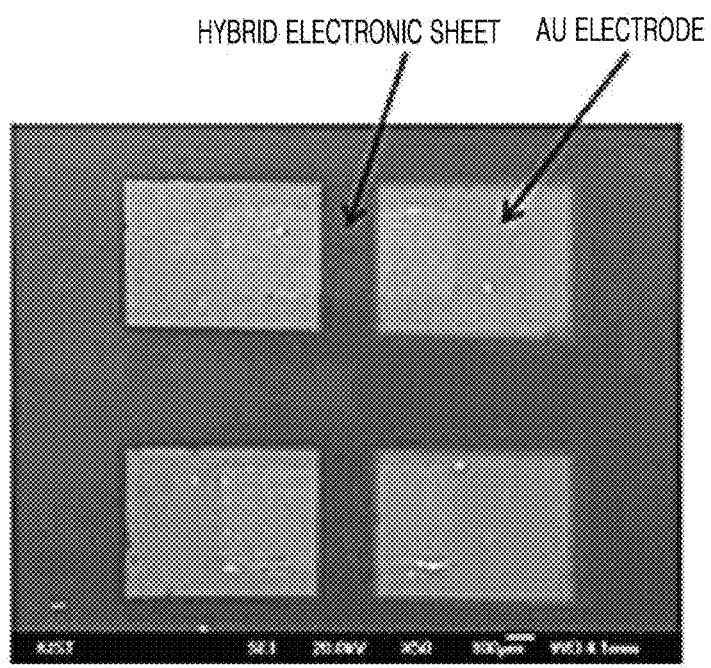
FIG. 12 is an SEM image of an electronic device which is prepared by using the hybrid electronic sheet according to an exemplary embodiment.

The hybrid electronic sheets prepared by mixing at a molar ratio of 1:2, 1:4, or 1:8 in Example 1.3.1 are transferred to a stencil mask, respectively and then deposited on $SiO_2$(300 nm)/Si substrate (manufacturer: SILTRON INC, product name: EPI-Prime Si wafer). After removing the stencil mask, the hybrid electronic sheets transferred onto the substrate are washed with deionized water and dried using nitrogen gas to prepare patterned hybrid electronic sheets. Then, a 100-nm Au electrode is formed as an electrode for measurement by sputtering using another stencil mask. FIG. 12 shows an SEM image thereof.

To compare electrical conductivity between three devices thus prepared, a back gate voltage is applied and a current-voltage (I-V) property is compared. The result of comparing the electrical conductivity is shown in FIG. 13.

FIG. 12 is an SEM image of an electronic device which is prepared by using the hybrid electronic sheet according to an exemplary embodiment.

As shown in FIG. 12, patterning of the hybrid electronic sheet according to an exemplary embodiment may be easily conducted using a substrate or a mask, and thus the sheet may be usefully applied to a flexible device.

Figure 13:
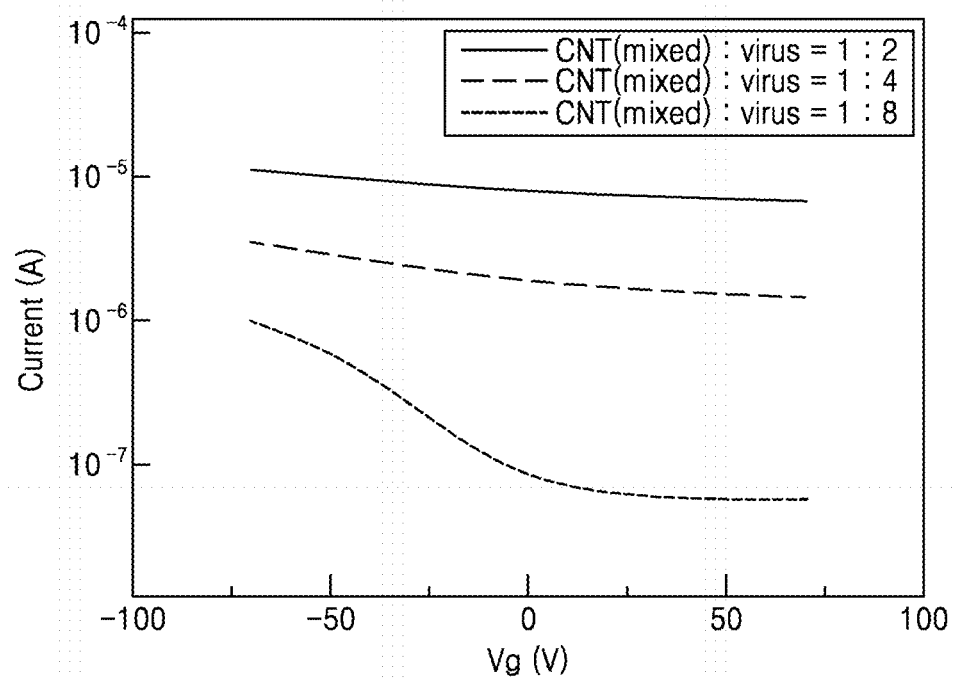
FIG. 13 is a graph showing electrical conductivity of the electronic device which is prepared by using the hybrid electronic sheet according to an exemplary embodiment.

FIG. 13 is a graph showing electrical conductivity of an electronic device which is prepared by using the hybrid electronic sheet according to an exemplary embodiment.

As shown in FIG. 13, the hybrid electronic sheet according to an exemplary embodiment exhibits p-type semiconductor properties because the current increases (i.e., resistance decreases) when the (−) gate voltage is applied. Also, better semiconductor property (on/off current ratio and off current) is observed as the molar ratio of the phage increases. This result indicates that since the hybrid single-walled carbon nanotube exhibits little tube bundling and semiconductor property near the threshold nanotube network density, the electrical conductivity of the electronic sheet may be controlled by controlling the mixing ratio of the carbon nanotube and the phage. Accordingly, the electronic sheet according to an exemplary embodiment is usefully applied to an information processing device or an information storing device.

2. Preparation of Hybrid Electronic Sheet 2

As another specific embodiment of the present invention, a hybrid electronic sheet is prepared in the same manner as in 1 of Example 1, except that the phage of 1.2 of Example 1 is prepared by a genetic recombination method as follows.

Primers of SEQ ID NOS. 14 and 15, and primers of SEQ ID NOS. 16 and 17 are used for M13 phage displaying the peptide of SEQ ID NO. 5 on p8 and M13 phage displaying the peptide of SEQ ID NO. 6 on p8 prepared by the genetic recombination method, respectively. In detail, annealing is performed at 95° C. for 2 minutes and cooling is performed to 25° C. at a rate of 0.1° C./s. Then, an M13HK vector is digested with the restriction enzymes BspHI and BamHI (after reaction with the enzymes at 37° C. for 2 hours, the enzymes are inactivated at 65° C. for 20 minutes) and then reacted T4 DNA ligase (NEB, product #M0202S) at 16° C. for 12 hours to obtain a circular vector. The ligated circular DNA is inserted into electro-competent $E.$ $coli$ (XL-1 Blue cell line, Agilent, product #200228) through electroporation, and genetically recombined M13 phage is amplified by culturing in a shaking incubator at 37° C. for 6 hours (following the instruction of the product manual for product #200228, Agilent). In order to purify the phage from the culture in which the phage and $E.$ $coli$ are mixed, the culture medium is centrifuged at 8000 rpm for 30 minutes and only the supernatant is taken. Since the phage is included in the supernatant, the separated supernatant is mixed with 20% w/v polyethylene glycol (Molecular weight 8000, Promega corporation, product #V3011)/NaCl solution, with a volume of ⅙ of that of the supernatant solution, and centrifuged at 12000 rpm for 30 minutes after reaction at 4° C. for about 16 hours. After discarding the supernatant from the resulting solution, the remaining phage thus precipitated is dissolved in Tris-buffered saline (TBS, Dako, product #S3001) to obtain a phage solution. In this regard, the concentration of the phage solution is calculated according to the following Equation 2.

$$\text{Phage concentration(viral particle/ml)} = 1.6 \times 10^{16} \times \text{O.D. viral solution}/7237 \quad \text{[Equation 2]}$$

The phage solution obtained by the above method may be amplified repeatedly using $E.$ $coli$. The phage is amplified using $E.$ $coli$ (XL-1 blue cell line) in early-log state (overnight culture diluted to 1/100). The amplified phage is purified in the same manner as described above.

3. Preparation of Hybrid Electronic Sheet 3

A hybrid electronic sheet is prepared using a mixture of a graphene sheet and a single-walled carbon nanotube as a graphitic material as follows.

3.1. Preparation of Colloid Solution

First, an aqueous solution is prepared by adding 2% w/v sodium cholate as a surfactant to distilled water, and a colloid solution is prepared by stabilizing a single-walled carbon nanotube (manufacturer:Nanointegris, SuperPure SWNTs, solution type, concentration: 250 mg/ml) and a graphene sheet (Nanointegris, PureSheets QUATTRO, solution type, concentration: 50 mg/ml) as graphitic materials with the sodium cholate by dialysis for 48 hours. In this regard, assuming that an average length and an average diameter of the carbon nanotube (CNT) are 1 μm and 1.4 nm, respectively, the number of the single-walled carbon nanotube included in the colloid solution is calculated as $7.5 \times 10^{13}$/mL according to Equation 1.

Further, the number of the graphene sheet may be calculated as follows.

(1) It is assumed that, since the graphene sheet (Puresheets QUATTRO, Nanointegris) is composed of single layers (6%), double layers (23%), triple layers (27%) and quadruple layers (44%), it is 3.09 layers on average.

(2) Since the area of the graphene unit lattice is about 0.0524 nm² and there are two carbon atoms per lattice, the area occupied by one carbon atom is 0.0262 nm².

(3) Since each graphene sheet has an average area of 10,000 nm², there are (10,000 nm²/0.0262 nm²)× 3.09=1.18×10⁶ carbon atoms per graphene sheet.

(4) An average weight of a graphene sheet is $\{1.18 \times 10^6/(6.02 \times 10^{23}\ \text{mol}^{-1})\} \times 12\ \text{g/mol} = 2.35 \times 10^{-17}$ g. Accordingly, the number of graphene sheets per 1 mg is $1 \times 10^{-6}$ g/$2.35 \times 10^{-17}$ g=$4.3 \times 10^{10}$.

Taken together, the following equation of calculating the number of the graphene sheet may be derived.

$$\text{Number of graphene nanotube}(/\text{mL}) = \text{concentration}\ (\mu\text{g/mL}) \times 4.3 \times 10^{10}\ \text{graphene} \quad \text{[Equation 3]}$$

Since the concentration of the graphene sheet (Puresheets QUATTRO) solution used in this Example is 50 μg/mL, it can be assumed that 1 mL of the solution contain $(50 \times 10^{-6}\ \text{g})/(2.35 \times 10^{-17}\ \text{g}) \approx 2.13 \times 10^{12}$ graphene sheets.

3.2. Preparation of Hybrid Electronic Sheet and Comparison of Electrochemical Property The colloid solution prepared as above and a phage solution prepared in 1.2 of Example 1 are mixed at a molar ratio of SWNT:graphene:p8GB#1(C:G:V)=10:2:1. Next, each of the mixtures is added to a semipermeable dialysis membrane (SpectrumLab, MWCO 12,000~14,000, product #132 700) tube and each membrane tube is dialyzed against triple distilled water. About 24 hours after the dialysis, a thin electronic sheet is formed along the surface of the membrane tube. Each membrane tube is added to triple distilled water and the electronic sheet is detached by twisting the membrane of the membrane tube and then dried. The prepared electronic sheet has a thickness of about 230 nm.

Electrochemical property is compared between the electronic sheet thus prepared and the hybrid electronic sheet prepared at a molar ratio of 10:1 in Example 1.3.1 in the same manner as in 1.6 of Example 1. The result is shown in FIG. 14.

Figure 14:
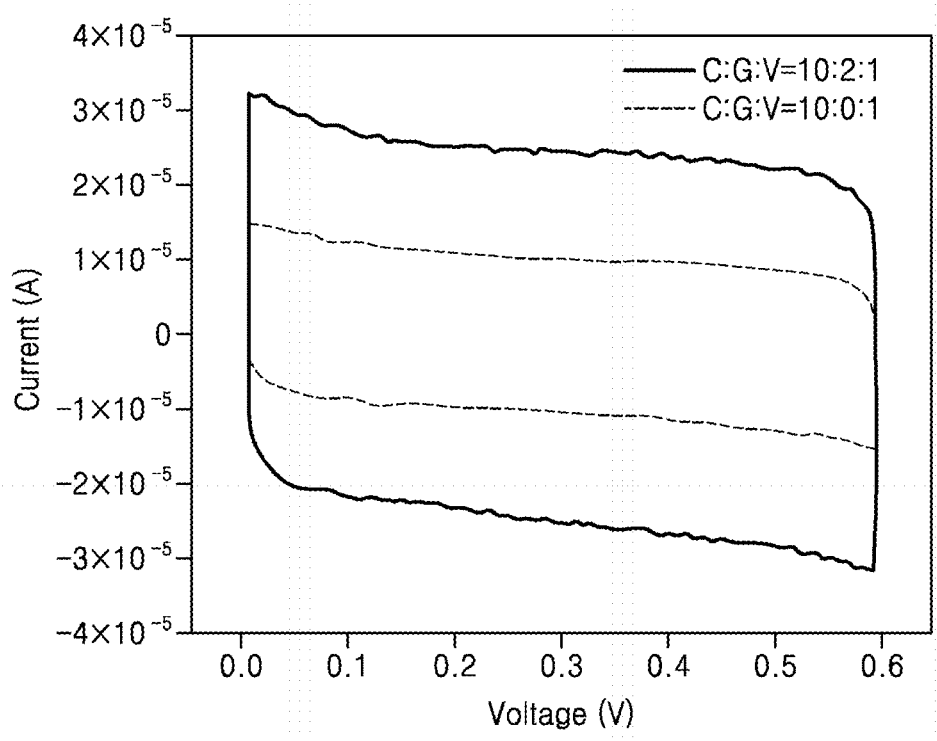
FIG. 14 is a graph showing electrochemical conductivity of the hybrid electronic sheet according to an exemplary embodiment.

FIG. 14 is a graph showing electrochemical conductivity of the hybrid electronic sheet according to an exemplary embodiment.

As shown in FIG. 14, compared to the electronic sheet prepared using a colloid solution containing only the single-walled carbon nanotube (C:G:V=10:0:1), the addition of graphene (C:G:V=10:2:1) resulted in increased sheet thickness and increased charging current per unit area.

4. Preparation of Hybrid Enzyme Electronic Sheet Functionalized with Biochemical Enzyme A hybrid enzyme electronic sheet including a biochemical enzyme and a nanoelectrode material is prepared as follows, and a biosensor electrode which is selective for an analyte and operates without a mediator that helps electron transport between the enzyme and the electrode is prepared using the same.

4.1. Preparation of Colloid Solution

First, an aqueous solution is prepared by adding 2% w/v sodium cholate as a surfactant to distilled water, and a colloid solution is prepared by stabilizing single-walled carbon nanotube with the sodium cholate by dialysis of carbon nanotube (manufacturer: Nanointegris, SuperPure SWNTs, solution-type, concentration: 250 mg/ml) for 48 hours.

In this regard, assuming that an average length and an average diameter of the carbon nanotube (CNT) are 1 μm and 1.4 nm, respectively, the number of the single-walled carbon nanotube included in the colloid solution may be calculated according to Equation 1. As a result, the number of the single-walled carbon nanotube is calculated as $7.5 \times 10^{13}$/mL.

4.2. Preparation of HRP-p8GB#1 Conjugate by Functionalization of p8GB#1 Phage with Biochemical Enzyme Horseradish Peroxidase (HRP)

The phage surface is functionalized with the enzyme HRP (Sigma-Aldrich, product #P8375-5KU) using 1-ethyl-3-(3-dimethylaminopropyl)carbodiimide (EDC) and N-hydroxysulfosuccinimide (sulfo-NHS). 4 mg of EDC (Sigma-Aldrich, product #E1769), 11 mg of sulfo-NHS (Sigma-Aldrich, product #56485), and 1 mg of P8GB#1 are mixed in 0.5 mL of 0.1 mM MES buffer (pH 6.0, Sigma-Aldrich) and reacted at room temperature for 30 minutes under mild shaking. Then, 1.4 μL of 2-mercaptoethanol (2ME; Pierce, product #35602) is added to stop the EDC reaction. Subsequently, after adding 0.5 mL of 0.1 M phosphate-buffered saline (PBS, pH 7.2) solution in which 1 mg of HRP is dissolved, the mixture is reacted overnight. Then, the reaction is stopped by adding hydroxylamine (Pierce, product #26103) to a final concentration of 10 mM. The HRP-functionalized p8GB#1 phage, i.e., HRP-p8GB#1 conjugate, is purified using PEG/NaCl as described in Example 1.

4.3. Preparation of Hybrid Enzyme Electronic Sheet Functionalized with Biochemical Enzyme The prepared colloid solution and a solution containing the prepared HRP-p8GB#1 are mixed at a molar ratio of 2:1. Then, the mixture is added to a semipermeable dialysis membrane (SpectrumLab, MWCO 12,000~14,000, product #132 700) tube and the membrane tube is dialyzed against triple distilled water with an ionic strength of 0.1 mM.

About 16 hours after the dialysis, a thin electronic sheet is formed along the surface of the membrane tube. The formed membrane tube is transferred to triple distilled water with an ionic strength of 0.1 mM and a freestanding hybrid enzyme electronic sheet is prepared by twisting the membrane of the membrane tube.

4.4. Selective Current Biosensor without Electron Mediator

The prepared freestanding hybrid enzyme electronic sheet is transferred onto an Au substrate and hydrogen peroxide is detected by current biosensing. HRP is an enzyme which reduces hydrogen peroxide ($H_2O_2$) to water ($H_2O$) and reacts selectively with hydrogen peroxide. Since the reduction occurs only when the enzyme receives an electron, the measured reduction current is proportional to the amount of hydrogen peroxide. The biosensing is conducted using the enzyme electronic sheet as a working electrode and using Pt wire and Ag/AgCl (3M KCl saturated, PAR, K0260) respectively as a counter electrode (PAR, K0266) and a reference electrode. Phosphate-buffered saline (0.1 M phosphate, 100 mM phosphate, pH=7.4) is used as an electrolyte. The measurement is made at a voltage fixed to −200 mV. Current is measured while injecting the analyte with 100-second intervals to a final concentration of 0.1 mM, and the result is shown in FIG. 15B.

Figure 15A:
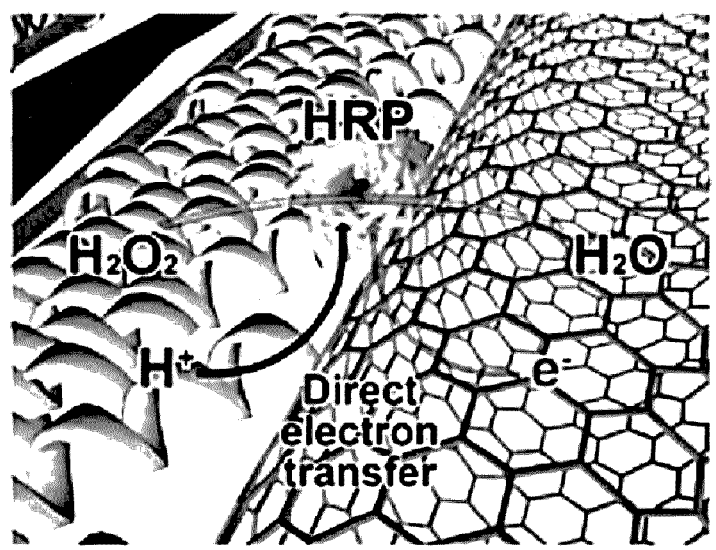
FIG. 15A is a schematic illustration of a current biosensing of a hybrid electronic sheet, in which the hybrid electronic sheet is functionalized with an enzyme according to an exemplary embodiment.
Figure 15B:
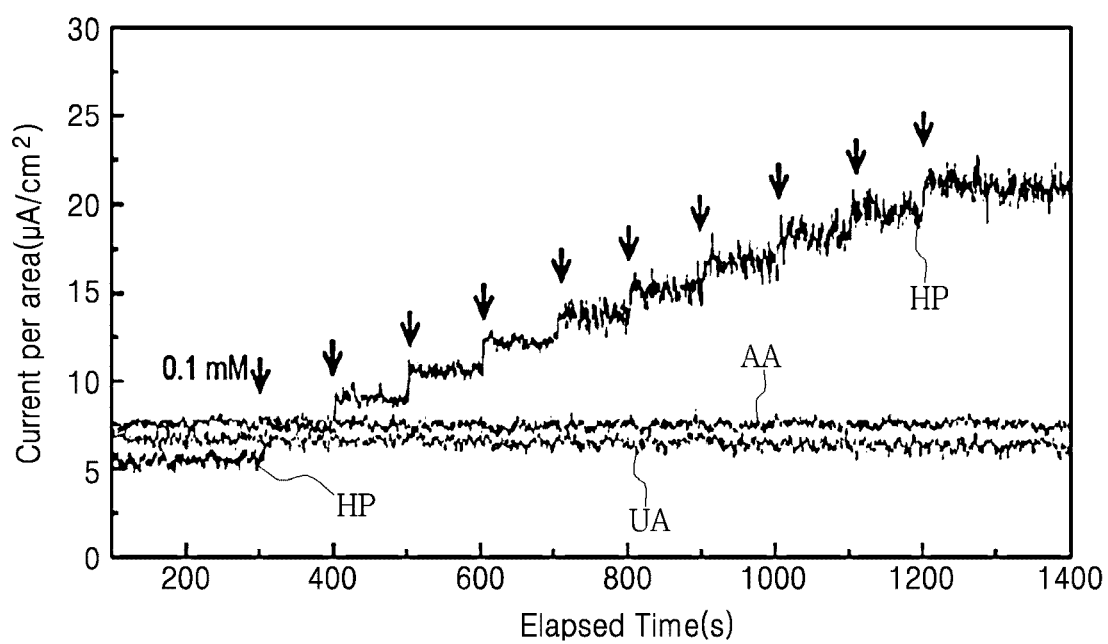
FIG. 15B is a graph showing selective current response of a biosensor to hydrogen peroxide, in which the biosensor includes the hybrid enzyme electronic sheet according to an exemplary embodiment.

FIG. 15A is a schematic illustration of a current biosensing of a hybrid electronic sheet, in which the hybrid electronic sheet is functionalized with an enzyme according to an exemplary embodiment.

As shown in FIG. 15A, when the hybrid electronic sheet functionalized with an enzyme according to an exemplary embodiment is used, it is possible to prepare a biosensor without an electron mediator.

As shown in FIG. 15A, direct electron transfer by oxidation-reduction of a substrate occurs in the hybrid electronic sheet functionalized with the enzyme according to an exemplary embodiment, and thus presence of the analyte (hydrogen peroxide) may be selectively detected.

FIG. 15B is a graph showing selective current response of a biosensor to hydrogen peroxide, in which the biosensor includes the hybrid enzyme electronic sheet according to an exemplary embodiment.

As shown in FIG. 15B, the enzyme electronic sheet functionalized with HRP enzyme responds only to hydrogen peroxide and does not respond to ascorbic acid and uric acid, which are widely known as interfering factors in current biosensing. It can be seen that hydrogen peroxide could be effectively detected without a mediator which is commonly used to improve the electron transport efficiency between the enzyme and the electrode.

A hybrid electronic sheet according to an aspect has superior electrochemical property and is transparent and flexible, and thus the sheet is transferred onto various substrates and used in a desired electrode or electronic device.

A method of preparing the hybrid electronic sheet according to an aspect may be used to transfer the sheet onto various substrates without a chemical etching process, and to easily form patterns.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An electronic sheet comprising:
a graphitic material; and
a phage binding to the graphitic material,
wherein the phage comprises a coat protein or a fragment thereof with a peptide displayed thereon, and the binding occurs between the graphitic material and the peptide,
wherein a C-terminus of the peptide is linked to an N-terminus of the coat protein of the phage, or the peptide is inserted between consecutive amino acid sequences of the coat protein of the phage or replaces the consecutive amino acid sequences of the coat protein.

2. The electronic sheet of claim 1, wherein the electronic sheet has an area of 0.0001 $cm^2$ to 1000 $cm^2$.

3. The electronic sheet of claim 1, wherein the electronic sheet has a thickness of 20 nm to 400 nm.

4. The electronic sheet of claim 1, wherein an internal structure of the electronic sheet has a percolated network structure.

5. The electronic sheet of claim 1, wherein the graphitic material is selected from the group consisting of a graphene sheet, a highly ordered pyrolytic graphite (HOPG) sheet, a single-walled carbon nanotube, a double-walled carbon nanotube, a multi-walled carbon nanotube, and fullerene.

6. The electronic sheet of claim 1, wherein the graphitic material comprises a graphene sheet and a single-walled carbon nanotube.

7. The electronic sheet of claim 1, wherein the peptide is selected from the group consisting of amino acid sequences of $X_2SX_{1.4}AX_2X_3P$ (SEQ ID NO. 1), $X_2X_2PX_3X_2AX_3P$ (SEQ ID NO. 2), $SX_{1.4}AX_2X_3P$ (SEQ ID NO. 3) and $X_2PX_3X_2AX_3P$ (SEQ ID NO. 4) and wherein $X_1$ is W, Y, F or H, $X_2$ is D, E, N or Q, and $X_3$ is I, L or V.

8. The electronic sheet of claim 7, wherein the peptide is selected from the group consisting SEQ ID No. 5, SEQ ID No. 6, SEQ ID No. 7, and SEQ ID No. 8.

9. The electronic sheet of claim 1, wherein the phage is genetically engineered and has a binding ability to the graphitic material.

10. The electronic sheet of claim 1, wherein the phage is a filamentous phage.

11. The electronic sheet of claim 10, wherein the phage is selected from the group consisting of M13 phage, F1 phage, Fd phage, If1 phage, Ike phage, Zj/Z phage, Ff phage, Xf phage, Pf1 phage, and Pf3 phage.

12. The electronic sheet of claim 1, wherein the C-terminus of the peptide is linked to the N-terminus of the coat protein of the phage.

13. The electronic sheet of claim 1, wherein the phage is conjugated with a biochemical enzyme.

14. An electrode comprising the electronic sheet of claim 1.

15. An electronic device comprising the electronic sheet of claim 1.

16. The electronic device of claim 15, wherein the electronic device is selected from the group consisting of a transparent electronic device, a flexible electronic device, an information processing device, an information storing device, a biosensor device, a bioelectrode device, and an energy device.

17. The electronic sheet of claim 1, wherein the peptide is inserted between consecutive amino acid sequences of the coat protein of the phage.

18. The electronic sheet of claim 1, wherein the peptide replaces the consecutive amino acid sequences of the coat protein.

19. An electronic sheet comprising:
a graphitic material; and
a phage binding to the graphitic material,
wherein the phage comprises a coat protein or a fragment thereof with a peptide displayed thereon, and the binding occurs between the graphitic material and the peptide,
wherein the phage is a filamentous phage;
wherein the phage is selected from the group consisting of M13 phage, F1 phage, Fd phage, If1 phage, Ike phage, Zj/Z phage, Ff phage, Xf phage, Pf1 phage, and Pf3 phage,
wherein the coat protein is selected from the group consisting of p3, p6, p8 and p9 of M13 phage.

20. An electronic sheet comprising:
a graphitic material selected from the group consisting of a graphene sheet, a highly ordered pyrolytic graphite (HOPG) sheet, a single-walled carbon nanotube, a double-walled carbon nanotube, a multi-walled carbon nanotube, and fullerene; and
a phage binding to the graphitic material, such that the phage comprises a coat protein or a fragment thereof with a peptide displayed thereon, and the binding occurs between the graphitic material and the peptide, wherein a C-terminus of the peptide is linked to an N-terminus of the coat protein of the phage, or the peptide is inserted between consecutive amino acid sequences of the coat protein of the phage or replaces the consecutive amino acid sequences of the coat protein;

wherein the peptide is selected from the group consisting SEQ ID No. 5, SEQ ID No. 6, SEQ ID No. 7, and SEQ ID No. 8.

* * * * *

SEQUENCE LISTING

<160> NUMBER OF SEQ ID NOS: 18

<210> SEQ ID NO 1
<211> LENGTH: 8
<212> TYPE: PRT
<213> ORGANISM: Artificial Sequence
<220> FEATURE:
<223> OTHER INFORMATION: peptide selectively binding to graphitic
      materials
<220> FEATURE:
<221> NAME/KEY: VARIANT
<222> LOCATION: (1)..(1)
<223> OTHER INFORMATION: X is D, E, N, or Q
<220> FEATURE:
<221> NAME/KEY: VARIANT
<222> LOCATION: (3)..(3)
<223> OTHER INFORMATION: X is W, Y, F or H
<220> FEATURE:
<221> NAME/KEY: VARIANT
<222> LOCATION: (6)..(6)
<223> OTHER INFORMATION: X is D, E, N or Q
<220> FEATURE:
<221> NAME/KEY: VARIANT
<222> LOCATION: (7)..(7)
<223> OTHER INFORMATION: X is I, L, or V

<400> SEQUENCE: 1

Xaa Ser Xaa Ala Ala Xaa Xaa Pro
1               5

<210> SEQ ID NO 2
<211> LENGTH: 8
<212> TYPE: PRT
<213> ORGANISM: Artificial Sequence
<220> FEATURE:
<223> OTHER INFORMATION: peptide selectively binding to graphitic
      materials
<220> FEATURE:
<221> NAME/KEY: VARIANT
<222> LOCATION: (1)..(1)
<223> OTHER INFORMATION: X is D, E, N, or Q
<220> FEATURE:
<221> NAME/KEY: VARIANT
<222> LOCATION: (2)..(2)
<223> OTHER INFORMATION: X is D, E, N, or Q
<220> FEATURE:
<221> NAME/KEY: VARIANT
<222> LOCATION: (4)..(4)
<223> OTHER INFORMATION: X is I, L, or V
<220> FEATURE:
<221> NAME/KEY: VARIANT
<222> LOCATION: (5)..(5)
<223> OTHER INFORMATION: X is D, E, N, or Q
<220> FEATURE:
<221> NAME/KEY: VARIANT
<222> LOCATION: (7)..(7)
<223> OTHER INFORMATION: X is I, L, or V

<400> SEQUENCE: 2

Xaa Xaa Pro Xaa Xaa Ala Xaa Pro
1               5

<210> SEQ ID NO 3
<211> LENGTH: 7
<212> TYPE: PRT
<213> ORGANISM: Artificial Sequence
<220> FEATURE:
<223> OTHER INFORMATION: peptide selectively binding to graphitic
      materials
<220> FEATURE:
<221> NAME/KEY: VARIANT
<222> LOCATION: (2)..(2)
<223> OTHER INFORMATION: X is W, Y, F, or H
<220> FEATURE:

<220> FEATURE:
<221> NAME/KEY: VARIANT
<222> LOCATION: (5)..(5)
<223> OTHER INFORMATION: X is D, E, N, or Q
<220> FEATURE:
<221> NAME/KEY: VARIANT
<222> LOCATION: (6)..(6)
<223> OTHER INFORMATION: X is I, L, or V

<400> SEQUENCE: 3

Ser Xaa Ala Ala Xaa Xaa Pro
1               5

<210> SEQ ID NO 4
<211> LENGTH: 7
<212> TYPE: PRT
<213> ORGANISM: Artificial Sequence
<220> FEATURE:
<223> OTHER INFORMATION: peptide selectively binding to graphitic
      materials
<220> FEATURE:
<221> NAME/KEY: VARIANT
<222> LOCATION: (1)..(1)
<223> OTHER INFORMATION: X is D, E, N, or Q
<220> FEATURE:
<221> NAME/KEY: VARIANT
<222> LOCATION: (3)..(3)
<223> OTHER INFORMATION: X is I, L, or V
<220> FEATURE:
<221> NAME/KEY: VARIANT
<222> LOCATION: (4)..(4)
<223> OTHER INFORMATION: X is D, E, N, or Q
<220> FEATURE:
<221> NAME/KEY: VARIANT
<222> LOCATION: (6)..(6)
<223> OTHER INFORMATION: X is I, L, or V

<400> SEQUENCE: 4

Xaa Pro Xaa Xaa Ala Xaa Pro
1               5

<210> SEQ ID NO 5
<211> LENGTH: 8
<212> TYPE: PRT
<213> ORGANISM: Artificial Sequence
<220> FEATURE:
<223> OTHER INFORMATION: peptide selectively binding to graphitic
      materials

<400> SEQUENCE: 5

Asp Ser Trp Ala Ala Asp Ile Pro
1               5

<210> SEQ ID NO 6
<211> LENGTH: 8
<212> TYPE: PRT
<213> ORGANISM: Artificial Sequence
<220> FEATURE:
<223> OTHER INFORMATION: peptide selectively binding to graphitic
      materials

<400> SEQUENCE: 6

Asp Asn Pro Ile Gln Ala Val Pro
1               5

<210> SEQ ID NO 7
<211> LENGTH: 7
<212> TYPE: PRT
<213> ORGANISM: Artificial Sequence
<220> FEATURE:
<223> OTHER INFORMATION: peptide selectively binding to graphitic
      materials

<400> SEQUENCE: 7

Ser Trp Ala Ala Asp Ile Pro
1               5

<210> SEQ ID NO 8
<211> LENGTH: 7
<212> TYPE: PRT
<213> ORGANISM: Artificial Sequence
<220> FEATURE:
<223> OTHER INFORMATION: peptide selectively binding to graphitic
      materials

<400> SEQUENCE: 8

Asn Pro Ile Gln Ala Val Pro
1               5

<210> SEQ ID NO 9
<211> LENGTH: 7222
<212> TYPE: DNA
<213> ORGANISM: Artificial Sequence
<220> FEATURE:
<223> OTHER INFORMATION: cloning vector M13KE

<400> SEQUENCE: 9

| | | | | | |
|---|---|---|---|---|---|
| aatgctacta | ctattagtag | aattgatgcc | acctttcag | ctcgcgcccc | aaatgaaaat | 60 |
| atagctaaac | aggttattga | ccatttgcga | aatgtatcta | atggtcaaac | taaatctact | 120 |
| cgttcgcaga | attgggaatc | aactgttata | tggaatgaaa | cttccagaca | ccgtacttta | 180 |
| gttgcatatt | taaaacatgt | tgagctacag | cattatattc | agcaattaag | ctctaagcca | 240 |
| tccgcaaaaa | tgacctctta | tcaaaaggag | caattaaagg | tactctctaa | tcctgacctg | 300 |
| ttggagtttg | cttccggtct | ggttcgcttt | gaagctcgaa | ttaaaacgcg | atatttgaag | 360 |
| tctttcgggc | ttcctcttaa | tctttttgat | gcaatccgct | ttgcttctga | ctataatagt | 420 |
| cagggtaaag | acctgatttt | tgatttatgg | tcattctcgt | tttctgaact | gtttaaagca | 480 |
| tttgagggg | attcaatgaa | tatttatgac | gattccgcag | tattggacgc | tatccagtct | 540 |
| aaacatttta | ctattacccc | ctctggcaaa | acttcttttg | caaaagcctc | tcgctatttt | 600 |
| ggtttttatc | gtcgtctggt | aaacgagggt | tatgatagtg | ttgctcttac | tatgcctcgt | 660 |
| aattcctttt | ggcgttatgt | atctgcatta | gttgaatgtg | gtattcctaa | atctcaactg | 720 |
| atgaatcttt | ctacctgtaa | taatgttgtt | ccgttagttc | gttttattaa | cgtagatttt | 780 |
| tcttcccaac | gtcctgactg | gtataatgag | ccagttctta | aaatcgcata | aggtaattca | 840 |
| caatgattaa | agttgaaatt | aaaccatctc | aagcccaatt | tactactcgt | tctggtgttt | 900 |
| ctcgtcaggg | caagccttat | tcactgaatg | agcagctttg | ttacgttgat | ttgggtaatg | 960 |
| aatatccggt | tcttgtcaag | attactcttg | atgaaggtca | gccagcctat | gcgcctggtc | 1020 |
| tgtacaccgt | tcatctgtcc | tctttcaaag | ttggtcagtt | cggttccctt | atgattgacc | 1080 |
| gtctgcgcct | cgttccggct | aagtaacatg | gagcaggtcg | cggatttcga | cacaatttat | 1140 |
| caggcgatga | tacaaatctc | cgttgtactt | tgtttcgcgc | ttggtataat | cgctggggt | 1200 |
| caaagatgag | tgttttagtg | tattcttttg | cctctttcgt | tttaggttgg | tgccttcgta | 1260 |
| gtggcattac | gtatttacc | cgtttaatgg | aaacttcctc | atgaaaaagt | ctttagtcct | 1320 |
| caaagcctct | gtagccgttg | ctaccctcgt | tccgatgctg | tctttcgctg | ctgagggtga | 1380 |
| cgatcccgca | aaagcggcct | ttaactccct | gcaagcctca | gcgaccgaat | atatcggtta | 1440 |
| tgcgtgggcg | atggttgttg | tcattgtcgg | cgcaactatc | ggtatcaagc | tgtttaagaa | 1500 |

```
attcacctcg aaagcaagct gataaaccga tacaattaaa ggctcctttt ggagcctttt      1560
ttttggagat tttcaacgtg aaaaaattat tattcgcaat tcctttagtg gtacctttct      1620
attctcactc ggccgaaact gttgaaagtt gtttagcaaa atcccataca gaaaattcat      1680
ttactaacgt ctggaaagac gacaaaactt tagatcgtta cgctaactat gagggctgtc      1740
tgtggaatgc tacaggcgtt gtagtttgta ctggtgacga aactcagtgt tacggtacat      1800
gggttcctat tgggcttgct atccctgaaa atgagggtgg tggctctgag ggtggcggtt      1860
ctgagggtgg cggttctgag ggtggcggta ctaaacctcc tgagtacggt gatacaccta      1920
ttccgggcta tacttatatc aaccctctcg acggcactta tccgcctggt actgagcaaa      1980
accccgctaa tcctaatcct tctcttgagg agtctcagcc tcttaatact ttcatgtttc      2040
agaataatag gttccgaaat aggcaggggg cattaactgt ttatacgggc actgttactc      2100
aaggcactga ccccgttaaa acttattacc agtacactcc tgtatcatca aaagccatgt      2160
atgacgctta ctggaacggt aaattcagag actgcgcttt ccattctggc tttaatgagg      2220
atttatttgt ttgtgaatat caaggccaat cgtctgacct gcctcaacct cctgtcaatg      2280
ctggcggcgg ctctggtggt ggttctggtg gcggctctga gggtggtggc tctgagggtg      2340
gcggttctga gggtggcggc tctgagggag gcggttccgg tggtggctct ggttccggtg      2400
attttgatta tgaaaagatg gcaaacgcta ataaggggc tatgaccgaa aatgccgatg      2460
aaaacgcgct acagtctgac gctaaaggca aacttgattc tgtcgctact gattacggtg      2520
ctgctatcga tggtttcatt ggtgacgttt ccggccttgc taatggtaat ggtgctactg      2580
gtgattttgc tggctctaat tcccaaatgg ctcaagtcgg tgacggtgat aattcacctt      2640
taatgaataa tttccgtcaa tatttacctt ccctccctca atcggttgaa tgtcgccctt      2700
ttgtctttgg cgctggtaaa ccatatgaat tttctattga ttgtgacaaa ataaacttat      2760
tccgtggtgt ctttgcgttt cttttatatg ttgccacctt tatgtatgta ttttctacgt      2820
ttgctaacat actgcgtaat aaggagtctt aatcatgcca gttcttttgg gtattccgtt      2880
attattgcgt ttcctcggtt tccttctggt aactttgttc ggctatctgc ttacttttct      2940
taaaaagggc ttcggtaaga tagctattgc tatttcattg tttcttgctc ttattattgg      3000
gcttaactca attcttgtgg gttatctctc tgatattagc gctcaattac cctctgactt      3060
tgttcagggt gttcagttaa ttctcccgtc taatgcgctt ccctgttttt atgttattct      3120
ctctgtaaag gctgctattt tcattttga cgttaaacaa aaaatcgttt cttatttgga      3180
ttgggataaa taatatggct gtttattttg taactggcaa attaggctct ggaaagacgc      3240
tcgttagcgt tggtaagatt caggataaaa ttgtagctgg gtgcaaaata gcaactaatc      3300
ttgatttaag gcttcaaaac ctcccgcaag tcgggaggtt cgctaaaacg cctcgcgttc      3360
ttagaatacc ggataagcct tctatatctg atttgcttgc tattgggcgc ggtaatgatt      3420
cctacgatga aaataaaaac ggcttgcttg ttctcgatga gtgcggtact tggtttaata      3480
cccgttcttg gaatgataag gaaagacagc cgattattga ttggtttcta catgctcgta      3540
aattaggatg ggatattatt tttcttgttc aggacttatc tattgttgat aaacaggcgc      3600
gttctgcatt agctgaacat gttgtttatt gtcgtcgtct ggacagaatt actttacctt      3660
ttgtcggtac tttatattct cttattactg gctcgaaaat gcctctgcct aaattacatg      3720
ttggcgttgt aaatatggc gattctcaat taagccctac tgttgagcgt tggctttata      3780
ctggtaagaa tttgtataac gcatatgata ctaaacaggc ttttttctagt aattatgatt      3840
```

-continued

```
ccggtgttta ttcttatttta acgccttatt tatcacacgg tcggtatttc aaaccattaa    3900
atttaggtca gaagatgaaa ttaactaaaa tatatttgaa aaagttttct cgcgttcttt    3960
gtcttgcgat tggatttgca tcagcattta catatagtta tataacccaa cctaagccgg    4020
aggttaaaaa ggtagtctct cagacctatg attttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200
ttaaaaaagg taattcaaat gaaattgtta aatgtaatta attttgtttt cttgatgttt    4260
gtttcatcat cttcttttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg caaataattt tgatatggta ggttctaacc cttccattat tcagaagtat    4500
aatccaaaca atcaggatta tattgatgaa ttgccatcat ctgataatca ggaatatgat    4560
gataattccg ctccttctgg tggttttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg gctctaatct attagttgtt    4740
agtgctccta agatattttt agataaccct cctcaattcc tttcaactgt tgatttgcca    4800
actgaccaga tattgattga gggttttgata tttgaggttc agcaaggtga tgctttagat    4860
ttttcatttg ctgctggctc tcagcgtggc actgttgcag gcggtgttaa tactgaccgc    4920
ctcacctctg ttttatcttc tgctggtggt tcgttcggta ttttttaatgg cgatgtttta    4980 gggctatcag ttcgcgcatt aaagactaat agccattcaa aaatattgtc tgtgccacgt    5040
attcttacgc tttcaggtca gaagggttct atctctgttg gccagaatgt tccttttatt    5100
actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa gaagtattgc tacaacggtt aatttgcgtg atggacagac tcttttactc    5340
ggtggcctca ctgattataa aaacacttct caggattctg gcgtaccgtt cctgtctaaa    5400 atcccttttaa tcggcctcct gtttagctcc cgctctgatt ctaacgagga aagcacgtta    5460
tacgtgctcg tcaaagcaac catagtacgc gccctgtagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt ccccgtcaag ctctaaatcg    5640
ggggctccct ttagggttcc gatttagtgc tttacggcac ctcgacccca aaaaacttga    5700
tttgggtgat ggttcacgta gtgggccatc gccctgatag acggtttttc gccctttgac    5760
gttggagtcc acgttcttta atagtggact cttgttccaa actggaacaa cactcaaccc    5820
tatctcgggc tattcttttg atttataagg gattttgccg atttcggaac caccatcaaa    5880
caggattttc gcctgctggg gcaaaccagc gtggaccgct tgctgcaact ctctcagggc    5940
caggcggtga agggcaatca gctgttgccc gtctcactgg tgaaaagaaa aaccaccctg    6000
gcgcccaata cgcaaaccgc ctctccccgc gcgttggccg attcattaat gcagctggca    6060
cgacaggttt cccgactgga aagcgggcag tgagcgcaac gcaattaatg tgagttagct    6120
cactcattag gcaccccagg ctttacactt tatgcttccg gctcgtatgt tgtgtggaat    6180
tgtgagcgga taacaatttc acacaggaaa cagctatgac catgattacg ccaagcttgc    6240
```

```
atgcctgcag gtcctcgaat tcactggccg tcgttttaca acgtcgtgac tgggaaaacc      6300
ctggcgttac ccaacttaat cgccttgcag cacatccccc tttcgccagc tggcgtaata      6360
gcgaagaggc ccgcaccgat cgcccttccc aacagttgcg cagcctgaat ggcgaatggc      6420
gctttgcctg gtttccggca ccagaagcgg tgccggaaag ctggctggag tgcgatcttc      6480
ctgaggccga tactgtcgtc gtcccctcaa actggcagat gcacggttac gatgcgccca      6540
tctacaccaa cgtgacctat cccattacgg tcaatccgcc gtttgttccc acggagaatc      6600
cgacgggttg ttactcgctc acatttaatg ttgatgaaag ctggctacag gaaggccaga      6660
cgcgaattat ttttgatggc gttcctattg gttaaaaaat gagctgattt aacaaaaatt      6720
taatgcgaat tttaacaaaa tattaacgtt tacaatttaa atatttgctt atacaatctt      6780
cctgtttttg gggcttttct gattatcaac cggggtacat gattgacat gctagtttt       6840 acgattaccg ttcatcgatt ctcttgtttg ctccagactc tcaggcaatg acctgatagc      6900
ctttgtagat ctctcaaaaa tagctaccct ctccggcatt aatttatcag ctagaacggt      6960
tgaatatcat attgatggtg atttgactgt ctccggcctt tctcaccctt ttgaatcttt      7020
acctacacat tactcaggca ttgcatttaa aatatgtgag ggttctaaaa attttttatcc     7080 ttgcgttgaa ataaaggctt ctcccgcaaa agtattacag ggtcataatg ttttttggtac     7140 aaccgattta gctttatgct ctgaggcttt attgcttaat tttgctaatt ctttgccttg      7200
cctgtatgat ttattggatg tt                                               7222
```

<210> SEQ ID NO 10
<211> LENGTH: 41
<212> TYPE: DNA
<213> ORGANISM: Artificial Sequence
<220> FEATURE:
<223> OTHER INFORMATION: BamH I_SM_upper which is a primer used for
      site-directed mutation

<400> SEQUENCE: 10

```
aaggccgctt ttgcgggatc ctcaccctca gcagcgaaag a                           41
```

<210> SEQ ID NO 11
<211> LENGTH: 41
<212> TYPE: DNA
<213> ORGANISM: Artificial Sequence
<220> FEATURE:
<223> OTHER INFORMATION: BamH I_SM_lower which is a primer used for
      site-directed mutation

<400> SEQUENCE: 11

```
tctttcgctg ctgagggtga ggatcccgca aaagcggcct t                           41
```

<210> SEQ ID NO 12
<211> LENGTH: 90
<212> TYPE: DNA
<213> ORGANISM: Artificial Sequence
<220> FEATURE:
<223> OTHER INFORMATION: BamM13HK_P8_primer which is an extension primer
      used for preparation

<400> SEQUENCE: 12

```
ttaatggaaa cttcctcatg aaaaagtctt tagtcctcaa agcctctgta gccgttgcta      60
ccctcgttcc gatgctgtct ttcgctgctg                                       90
```

<210> SEQ ID NO 13
<211> LENGTH: 95

```
<212> TYPE: DNA
<213> ORGANISM: Artificial Sequence
<220> FEATURE:
<223> OTHER INFORMATION: M13HK_P8 which is a library oligonucleotide
      used for preparation
<220> FEATURE:
<221> NAME/KEY: misc_feature
<222> LOCATION: (1)..(95)
<223> OTHER INFORMATION: n is a, g, c or t
<220> FEATURE:
<221> NAME/KEY: misc_feature
<222> LOCATION: (1)..(95)
<223> OTHER INFORMATION: m is a or c

<400> SEQUENCE: 13
aaggccgctt ttgcgggatc cnnmnnmnnm nnmnnmnnmn nmncagcagc gaaagacagc      60
atcggaacga gggtagcaac ggctacagag gcttt                                95

<210> SEQ ID NO 14
<211> LENGTH: 97
<212> TYPE: DNA
<213> ORGANISM: Artificial Sequence
<220> FEATURE:
<223> OTHER INFORMATION: insert for coding a peptide having binding
      affinity to graphitic materials

<400> SEQUENCE: 14
catgaaaaag tcttttgtcc tcaaagcctc tgtagccgtt gctaccctcg ttccgatgct      60
gtctttcgct gctgattctt gggctgcgga tattccg                               97

<210> SEQ ID NO 15
<211> LENGTH: 97
<212> TYPE: DNA
<213> ORGANISM: Artificial Sequence
<220> FEATURE:
<223> OTHER INFORMATION: insert for coding a peptide having binding
      affinity to graphitic materials

<400> SEQUENCE: 15
gatccggaat atccgcagcc caagaatcag gcagcgaaag acagcatcgg aacgagggta      60
gcaacggcta cagaggcttt gaggacaaag acttttt                               97

<210> SEQ ID NO 16
<211> LENGTH: 97
<212> TYPE: DNA
<213> ORGANISM: Artificial Sequence
<220> FEATURE:
<223> OTHER INFORMATION: insert for coding a peptide having binding
      affinity to graphitic materials

<400> SEQUENCE: 16
catgaaaaag tcttttgtcc tcaaagcctc tgtagccgtt gctaccctcg ttccgatgct      60
gtctttcgct gctgataatc cgattcaggc tgttccg                               97

<210> SEQ ID NO 17
<211> LENGTH: 97
<212> TYPE: DNA
<213> ORGANISM: Artificial Sequence
<220> FEATURE:
<223> OTHER INFORMATION: insert for coding a peptide having binding
      affinity to graphitic materials

<400> SEQUENCE: 17
gatccggaac agcctgaatc ggattatcag gcagcgaaag acagcatcgg aacgagggta      60
gcaacggcta cagaggcttt gaggacaaag acttttt                               97
```

```
<210> SEQ ID NO 18
<211> LENGTH: 50
<212> TYPE: PRT
<213> ORGANISM: Artificial Sequence
<220> FEATURE:
<223> OTHER INFORMATION: P8 protein of M13 phage

<400> SEQUENCE: 18

Ala Glu Gly Asp Asp Pro Ala Lys Ala Ala Phe Asn Ser Leu Gln Ala
1               5                   10                  15

Ser Ala Thr Glu Tyr Ile Gly Tyr Ala Trp Ala Met Val Val Val Ile
            20                  25                  30

Val Gly Ala Thr Ile Gly Ile Lys Leu Phe Lys Lys Phe Thr Ser Lys
        35                  40                  45

Ala Ser
    50
```